(12) United States Patent
Yoon et al.

(10) Patent No.: US 7,673,528 B2
(45) Date of Patent: Mar. 9, 2010

(54) FLEXIBLE MODULAR SENSOR SYSTEMS

(76) Inventors: Euisik Yoon, 3340 Zircon La. N., Plymouth, MN (US) 55447; Hyung-Kew Lee, 4-166 EE/Csci Bldg, 200 Union St. SE., Minneapolis, MN (US) 55455

( * ) Notice: Subject to any disclaimer, the term of this patent is extended or adjusted under 35 U.S.C. 154(b) by 527 days.

(21) Appl. No.: 11/382,695

(22) Filed: May 10, 2006

(65) Prior Publication Data

US 2006/0254369 A1    Nov. 16, 2006

Related U.S. Application Data

(60) Provisional application No. 60/762,649, filed on Jan. 28, 2006.

(30) Foreign Application Priority Data

| May 12, 2005 | (KR) | ............ 10-2005-0039803 |
| May 26, 2005 | (KR) | ............ 10-2005-0044570 |

(51) Int. Cl.
*G01D 7/00* (2006.01)
(52) U.S. Cl. ............................................. 73/862.041
(58) Field of Classification Search ................. 73/862.041–862.046
See application file for complete search history.

(56) References Cited

U.S. PATENT DOCUMENTS

| 4,748,812 | A  | * | 6/1988 | Okada et al. .................. 60/614 |
| 5,760,530 | A  | * | 6/1998 | Kolesar ....................... 310/339 |
| 6,216,545 | B1 | * | 4/2001 | Taylor ....................... 73/862.046 |
| 6,769,313 | B2 | * | 8/2004 | Weiss ........................ 73/862.046 |
| 2004/0176818 | A1 | | 9/2004 | Wahlstrand |
| 2004/0259391 | A1 | | 12/2004 | Jung |
| 2005/0029680 | A1 | | 2/2005 | Jung |

OTHER PUBLICATIONS

Kawaguchi, Cut-and-Paste Customization of Organic FET Integrated Circuit and Its Application to Electronic Artificial Skin, IEEE Journal of Solid-State Circuits, vol. 40, No. 1, Jan. 2005, pp. 177-185.
Pan, A Flexible Full-body Tactile Sensor of Low Cost and Minimal Connections, 2003 IEEE, pp. 2368-2373.

(Continued)

*Primary Examiner*—Lisa M Caputo
*Assistant Examiner*—Octavia Davis
(74) *Attorney, Agent, or Firm*—Craig Taylor Law Office, PLLC

(57) ABSTRACT

Sensor systems, methods of making sensor modules and circuit modules, and methods of making expanded sensor systems including the sensor modules and circuit modules. A sensor module can include a flexible substrate, internal conductor lines, edge conductor lines for module interconnection, and sensors integrated thereon. One sensor module includes an array of interconnected capacitive pressure tactile sensors (taxels), being row addressable from address lines and readable through data lines. The sensor modules can be bonded to each other to form a larger array of sensors. One bonding method utilizes anisotropic conductive paste (ACP). The sensor system provided can be flexible and easy to expand to cover large areas. By using various sensor modules, the sensor system can be used for various applications. Readout modules can be coupled to the exterior edges to read all the individual sensors. Applications include robotic skin and wearable sensor fabrics.

6 Claims, 23 Drawing Sheets

OTHER PUBLICATIONS

Eltaib, Tactile sensing technology for minimal access surgery—a review, Mechatronics 13 (2003) pp. 1163-1177.

Marculescu, Electronic Textiles: A Platform for Pervasive Computing, Proceedings of the IEEE, vol. 91, No. 12, Dec. 2003, pp. 1995-2018.

Lee, Tactile Sensing for mechatronics—a state of art survey, Mechatronics, 9, pp. 1-31, 1999.

Sergio, A Textile Based Capacitive Pressure Sensor, Proceedings of IEEE Sensors, vol. 2, Jun. 12-14, 2002, pp. 1625-1630.

Mei, An Integrated MEMS three dimensional tactile sensor with large force range, Sensors and Actuators A, vol. 80, pp. 155-162, 2000.

Engel, Development of polyimide flexible tactile sensor skin, J. of Micromechanics and Microengineering, vol. 13, pp. 359-366, 2003.

Byung-Ho, Three Dimensional Micro-Channel Fabrication in Polydimethylsiloxane (PDMS) Elastomer, J. Microelectromech. Syst., vol. 9, No. 1, pp. 76-81, 2000.

Jung, Enabling technologies for disappearing electronics in smart textiles, Infeneon Technology AG, ISSCC 2003.

Chen, Development of Polymer-based Artificial Haircell Using Surface Micromachining and 3D Assembly, Transducers '03, The 12th Intl Conf. on Solid State Sensors, Actuators and Microsystems, Boston, Jun. 8-12, 2003.

\* cited by examiner (a) Readout chip bonding using ACP (b) Integrated readout chip on PDMS substrate & bonded site (a), (b) Photograph of fabricated polymer substrate with metal lines and bumps, (c) photograph of flip-bonded chip (backside) and (d) magnified view of ACP.

(a) Photograph of the flip-bonded chip on polymer substrate and (b) a captured 8x8 image of characters 'IML' from the fabricated tactile sensor array assembled with readout circuit chips.

Schematic diagram of the proposed modular expandable tactile sensor: (a) sensor module array, (b) one sensor module and (c) structure of single tactile cell in a sensor module.

Cross-sectional view of a tactile cell and its dimensions.

*Fabrication process of the proposed tactile sensor module: (a) Electrode layer, (b) Insulation and spacer layers, (c) bump layer process, (d) bonding sequence and (e) the completed device.*

*(a) Fabricated tactile sensor module, (b) magnified view of cells and (c) bottom electrodes and spacer layer of four tactile cells.*

Measurement setup for single cell characterization.

Measured response of the fabricated tactile sensor cells with thickness variation.

(a)

(b)
*Schematic of readout circuits for the fabricated sensor module.*

*Flipped photographs of rubber stamps and their tactile images captured by the fabricated tactile sensor module*

(a) Expanded tactile sensor module in 2x2 modular array, (b) module to module bonding by using ACP, and (c) measured tactile image of a character 'O' using the 2x2 expanded sensor module.

FLEXIBLE MODULAR SENSOR SYSTEMS

RELATED APPLICATIONS

The present invention is a non-provisional patent application of U.S. Provisional Patent Application No. 60/762,649, filed Jan. 28, 2006, and claims priority to Korean National Patent Applications KR 10-2005-0039802, filed May 12, 2005, and KR 10-2005-0044570, filed May 26, 2005.

FIELD OF INVENTION

The present invention is related generally to sensors. More specifically, the present invention is related to systems and methods for joining groups of multiple flexible sensors to cover larger areas. The invention can be used to form tactile sensitive robot skin and flexible, wearable electrically coupled tactile sensors.

BACKGROUND

Many researchers have been conducting research to integrate electronic device functions (and functionality) such as MP3 players, computers, and health monitoring sensor systems into flexible packaging, for example, into clothes. Research into flexible electronics generally, such as flexible displays, has also been pursued. Key challenging technologies include implementing flexible electronic modules and connecting them. In one example, Infineon Technology in Germany presented a work titled "Enabling Technologies for Disappearing Electronics in Smart Textiles" at ISSCC 2003.

Research into ubiquitous sensor systems which consist of a large a network of sensor modules that can sense, process, and transmit various signals has been conducted. Some commercial products are currently available. The concept was summarized and presented at the 2004 International Conference on Applications and the Internet, in a paper titled "Ubiquitous Services and Networking: Monitoring the Real World."

These technologies have tremendous potential. According to these technology trends, implementing a flexible and independent system of various functions by connecting flexible functional modules may likely be a key technology in the near future.

What would be desirable are improved methods and systems for creating sensors which cover larger, expanded areas by joining smaller sensors into groups.

SUMMARY

The present invention provides a sensor system comprising: a circuit module comprised of a first flexible substrate, a plurality of routing conductor lines, a plurality of interconnection conductor lines, IC chips integrated on the first flexible substrate; and a sensor module comprised of a second flexible substrate on which routing conductor lines and a plurality of interconnection conductor lines are formed, having sensors integrated on the substrate, wherein the sensor module and circuit module are electrically coupled to each other. In some sensor systems, the sensor modules and circuit modules are directly connected to each other with anisotropic conductive paste (ACP), or other electrical bonding methods. The sensor modules and circuit modules may be indirectly connected to each other through ACP bonded to a flexible connection module. In other embodiments, at least two sensor modules and two circuit modules are connected to each other electrically. The sensor modules may be arranged as a matrix having 2 dimensions to form exterior edges, the circuit modules attached to at least one exterior edge along each dimension, and at least one circuit module attached at a corner of the matrix where the two exterior edges meet, so that all the circuit modules are electrically connected. The substrate may be flexible polymer.

The present invention also provides a sensor device comprising: a plurality of sensor modules with the sensor modules including a plurality of sensors on a flexible substrate, the sensors configured to measure a physical property and to output data corresponding to the measured data, the sensors being coupled to a plurality of address lines for selecting the sensors and coupled to a plurality of data lines for reading the sensor data. The sensor device also includes the sensor modules having edge address conductors and edge data conductors. The device has the sensor modules grouped adjacent to each other, the device having adjacent address edge conductors electrically coupled together, the device having adjacent data edge conductors electrically coupled together, such that at least some sensor module edges remain on an exterior of the module grouping which are not between adjacent sensor modules. There exists sensors within the sensor modules that can be addressed through adjacent interposed sensor module address lines and have data that can be read through adjacent interposed sensor module data lines.

The sensor device can further have addressing circuitry electrically coupled to at least some sensor module exterior edge address conductors. The device may also have readout circuitry electrically coupled to at least some sensor module exterior edge data conductors and measurement circuitry electrically coupled to at least some sensor module exterior edge data conductors. The device may also include control circuitry coupled to the addressing circuitry and to the measurement circuitry for controlling the addressing of the sensors and for reading the data from the selected sensors. In some devices, at least some of the sensors generate analog data signals having a range of possible values. At least some of the sensors may generate binary data signals and/or serial digital signals. At least some of the adjacent edge conductors may overlap and be joined using ACP.

In some sensor devices, at least some of the adjacent edge conductors are joined with a flexible joining module which overlaps the adjacent edge conductors and is electrically coupled to the adjacent edge conductors and which establishes electrical continuity between the adjacent edge conductors. The sensors may be selected for reading at least in part by reading data from the sensor. The sensor modules can be arranged in rows and/or columns, in some devices. At least some of the sensors are pressure sensors.

In some sensor devices, the sensors include pressure sensors including a first, flexible plate conductor supported in spaced part relation to a second plate conductor and having a compressible dielectric therebetween, forming a capacitor between the two plates, such that increasing deflection of the first plate towards the second plate increases the capacitance of the capacitor. The compressible dielectric is a gas, which may be air. The gas may exit from between the two plates in response to the increased deflection, in some devices. The gas may exit into other capacitors, in some embodiments, and may be sealed or open to the outside atmosphere, depending on the embodiments.

In some sensor devices, the address lines serve to address a set including a plurality of sensors at the same time, and the data lines serve to read out data from the addressed sensors. The address lines may select a row of sensors, where the data lines select individual sensors from the selected row by reading the data from the individual sensors. The data read can include capacitance values from the sensors selected and read through the data lines. At least some of the plates may include electrically conductive material bonded to an electrically insulating polymer. At least some of the sensor modules may have sensors for measuring different physical properties and/or different ranges of those properties within the same sensor. Sensors may be selected from the group consisting of pressure, optical, temperature, continuity, pH, humidity, ion concentration, and combinations thereof, depending on the embodiment.

The present invention also provides methods for making the sensors, sensor modules, other modules, and systems made of these modules. One method includes: grouping a plurality of flexible sensor modules having edge conductors into adjacent locations to each other; and physically bonding adjacent electrical conductors into electrically continuity with each other, such that the grouped plurality of flexible sensor modules remain flexible. The method may have the bonding accomplished using Anistropic Conductive Paste (ACP). The grouping may include overlapping adjacent edge conductors with each other, and in which the bonding includes bonding the overlapping edge conductors. The grouping can include overlapping adjacent edge conductors with a flexible joining connector, where the flexible joining connector is configured to establish electrical continuity between adjacent edge conductors which the joining connector overlaps, and in which the bonding includes bonding the overlapping joining connector to the edge conductors.

The sensor system described in this invention can be applied where flexible and expandable sensor systems are required. Depending on the sensors used, the system can be applied in various fields. For example, if a tactile sensor is used, the system can be used for robot skin, for example, to provide touch, to sense being touched, and to be used on the feet to assist in balance and walking. If a pressure sensor array is used, measuring pressure distribution as applied to human feet when walking will be possible, for medical purposes, prosthetic purposes, and the like. Medical sensors can be used, for example, to make a health monitoring cloth having temperature and pressure sensors combined.

The present invention can includes a modular expandable sensor system which can be deployed on a curved surface in any size by stitching functional modules for artificial skin for robots, smart clothes which can monitor human body status, wearable computers, or any other applications where a large flexible sensor array may be deployed. These modules may be implemented using a flexible polymer platform, and the sensor system can be deployed on any curved surface such as robot or human bodies. A sensor can be integrated in this sensor system for itself or in combination with other kinds of sensors.

The present invention can provide an electrode layer for capacitors having high flexibility and a method of manufacturing the electrode layer. The present invention can also provide a unit sensor that can be easily manufactured while the unit sensor has high flexibility and resolution. The present invention can further provide a tactile sensor having high flexibility and easy extendability.

In accordance with one aspect of the present invention, some devices can be made by the provision of an electrode layer for capacitors whose capacitance is changed depending upon the variation in distance between two electrode layers, wherein the electrode layers comprise: a polymer substrate; an electrode formed on the polymer substrate; and a signal transmission line formed on the polymer substrate, such that the signal transmission line is connected to the electrode.

In accordance with another aspect of the present invention, there is provided a method of manufacturing an electrode layer for capacitors, wherein the method comprises the steps of: forming a sacrifice layer on a silicon substrate; forming an electrode and a signal transmission line at a predetermined area on the sacrifice layer; coating the sacrifice layer (on which the electrode and the signal transmission line are formed) with liquid-state polymer, and hardening the liquid-state polymer; and removing the silicon substrate and the sacrifice layer.

In accordance with another aspect of the present invention, there is provided a unit sensor comprising: an upper electrode layer including a polymer substrate, an upper electrode formed on the polymer substrate, and a signal transmission line formed on the polymer substrate, such that the signal transmission line extends in the side-to-side direction of the upper electrode. The sensor also includes a lower electrode layer including a polymer substrate, a lower electrode formed on the polymer substrate, and a signal transmission line formed on the polymer substrate such that the signal transmission line extends in the front-to-rear direction of the lower electrode. The sensor further includes a spacer layer, made of polymer and disposed between the upper electrode layer and the lower electrode layer, the spacer layer being provided at a predetermined area thereof with an opening, through which the upper electrode and the lower electrode face each other.

In some embodiments, the unit sensor also comprises an insulating layer, made of polymer, disposed between the upper electrode layer and the spacer layer. Alternatively, the insulating layer may be disposed between the lower electrode layer and the spacer layer. The unit sensor may further comprise a bump layer, made of polymer, disposed on the upper electrode layer.

In accordance with yet another aspect of the present invention, there is provided a tactile sensor comprising: a unit sensor array including a plurality of unit sensors formed in a two-dimensional array, the upper electrodes of the unit sensors being electrically connected with each other by the sequential interconnection of the signal transmission lines for the upper electrodes, the lower electrodes of the unit sensors being electrically connected with each other by the sequential interconnection of the signal transmission lines for the lower electrodes. The sensor can also include connection lines disposed at the ends of the signal transmission lines for the upper electrodes and the signal transmission lines for the lower electrodes to connect the unit sensor array to the outside.

Some embodiments of the present invention provide a fabrication method of a circuit module which includes: preparing a silicon wafer as a carrier; coating a sacrificial layer on the silicon wafer; forming routing lines and interconnection lines on the sacrificial layer; and coating and curing a polymer layer on the sacrificial layer to make a flexible substrate. The method also includes removing the sacrificial layer to peel off the completed flexible substrate; forming an insulation layer on the routing lines except where any IC chips are to be bonded; and bonding IC chips on the flexible substrate. In some of these methods, a step forming a bump mold by etching part of sacrificial layer is included after forming the sacrificial layer, and bumps are formed during electroplating for interconnection lines. In some such methods, the IC chips include bumps for integration.

Some embodiment sensor module fabrication methods can include preparing a silicon wafer as a carrier; coating a sacrificial layer on the silicon wafer; forming a plurality of routing lines and interconnection lines on the sacrificial layer; and coating and curing a polymer layer on the sacrificial layer to make a flexible substrate. The method also includes removing the sacrificial layer to peel off the completed flexible substrate; forming an insulation layer on the routing lines except where the sensors are to be bonded; and bonding sensors on the flexible substrate. Such methods may also include a step forming a bump mold by etching part of the sacrificial layer after forming the sacrificial layer, where bumps are formed during electroplating for interconnection lines. In some methods, the sensors include bumps for integration.

A fabrication method of a sensor is provided in some embodiments, which includes: preparing a silicon wafer as a carrier; coating a sacrificial layer on the silicon wafer; forming routing lines and interconnection lines on the sacrificial layer; and coating and curing structure polymer to make a flexible substrate. The method also includes removing sacrificial layer to peel off the completed flexible substrate, and forming an insulation layer on the routing lines except where the IC chips and sensors are bonded, and bonding IC chips and sensors on the flexible substrate. The method may also include a step forming a bump mold by etching part of the sacrificial layer after forming the sacrificial layer, and bumps are formed during electroplating for interconnection lines. In some methods, IC chips and sensors include bumps for integration.

DETAILED DESCRIPTION

Figure 1A:
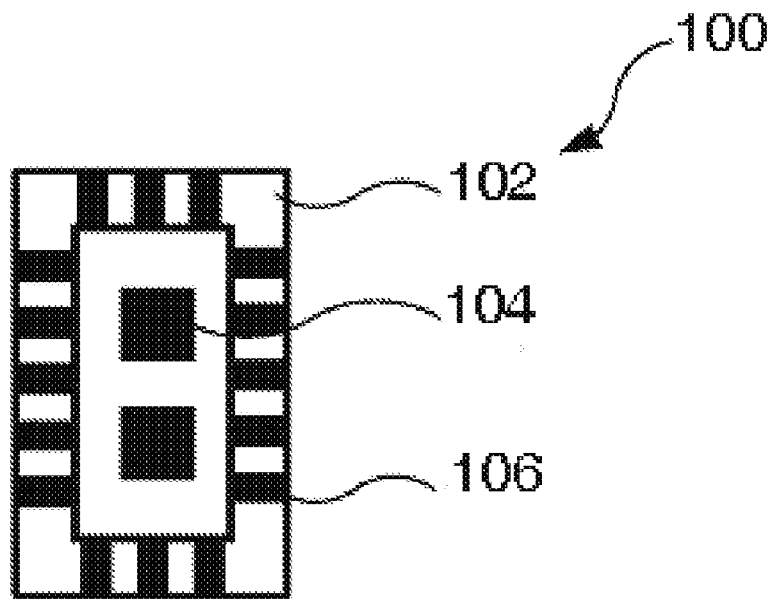
FIG. 1A is a high level diagram of an interface circuit module which can be used to interface to a sensor module.

FIG. 1A illustrates a circuit module 100 which is comprised of a substrate 102 on which routing lines and interconnection lines 106 are formed and IC chips 104 that are integrated on the substrate 102. FIG. 1A illustrates the circuit module with integrated IC chips. Substrate 102 can be made of rubbers, polyimides, or other polymers for flexibility. The routing lines, and interconnection lines 106 can be formed by electroplating and connected electrically. IC chips or integrated circuits 104 can be integrated on the substrate using anisotropic conductive paste (ACP). In order to integrate chips 104, the substrate or IC chips 104 can have bumps. Multiple routing lines may be formed on substrate 102.

Figure 1B:
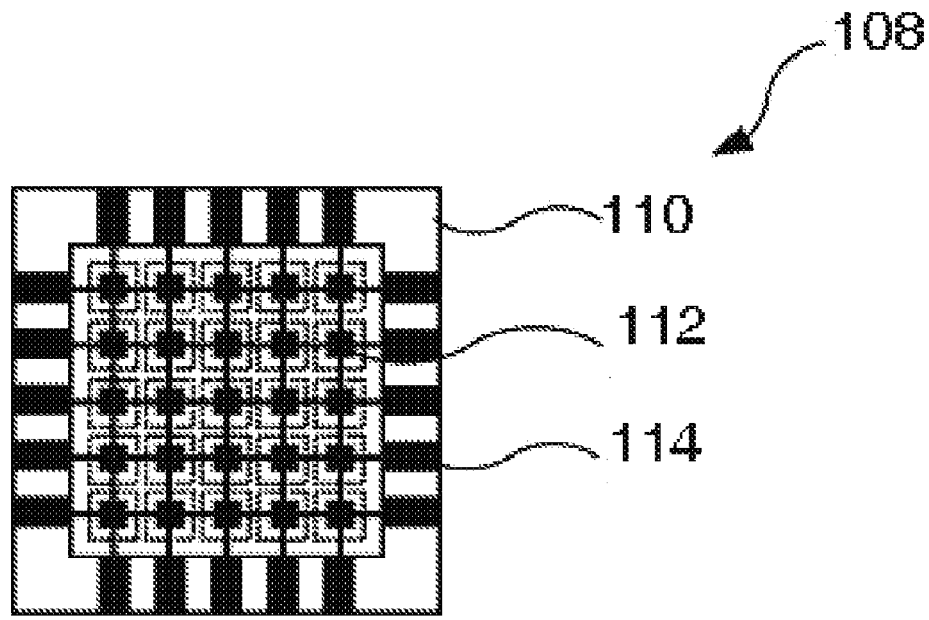
FIG. 1B is a high level diagram of a tactile sensor module having an array of taxels and edge row and column pad conductors for connecting to other tactile sensor modules and for connecting to interface circuits.

FIG. 1B illustrates a sensor module 108 which is comprised of a substrate 110 on which routing lines and interconnection lines 112 are formed, and sensors 112 that are integrated on substrate 110. Like circuit module 100, the substrate 110 can be made of polymers, and the routing lines and interconnection lines 114 can be formed by electroplating. Sensors 112 can be integrated on substrate 110 using anisotropic conductive paste, in some embodiments. In order to integrate sensors 112, the substrate 110 or sensors 112 can have bumps.

According to a first embodiment, a sensor system is formed by connecting circuit modules 100 and sensor modules 108 through interconnection lines 114. The connection can be done by attaching modules directly or indirectly using an anisotropic conductive paste or by attaching modules using other flexible connection modules that contain interconnection lines and using an anisotropic conductive paste.

Figure 2:
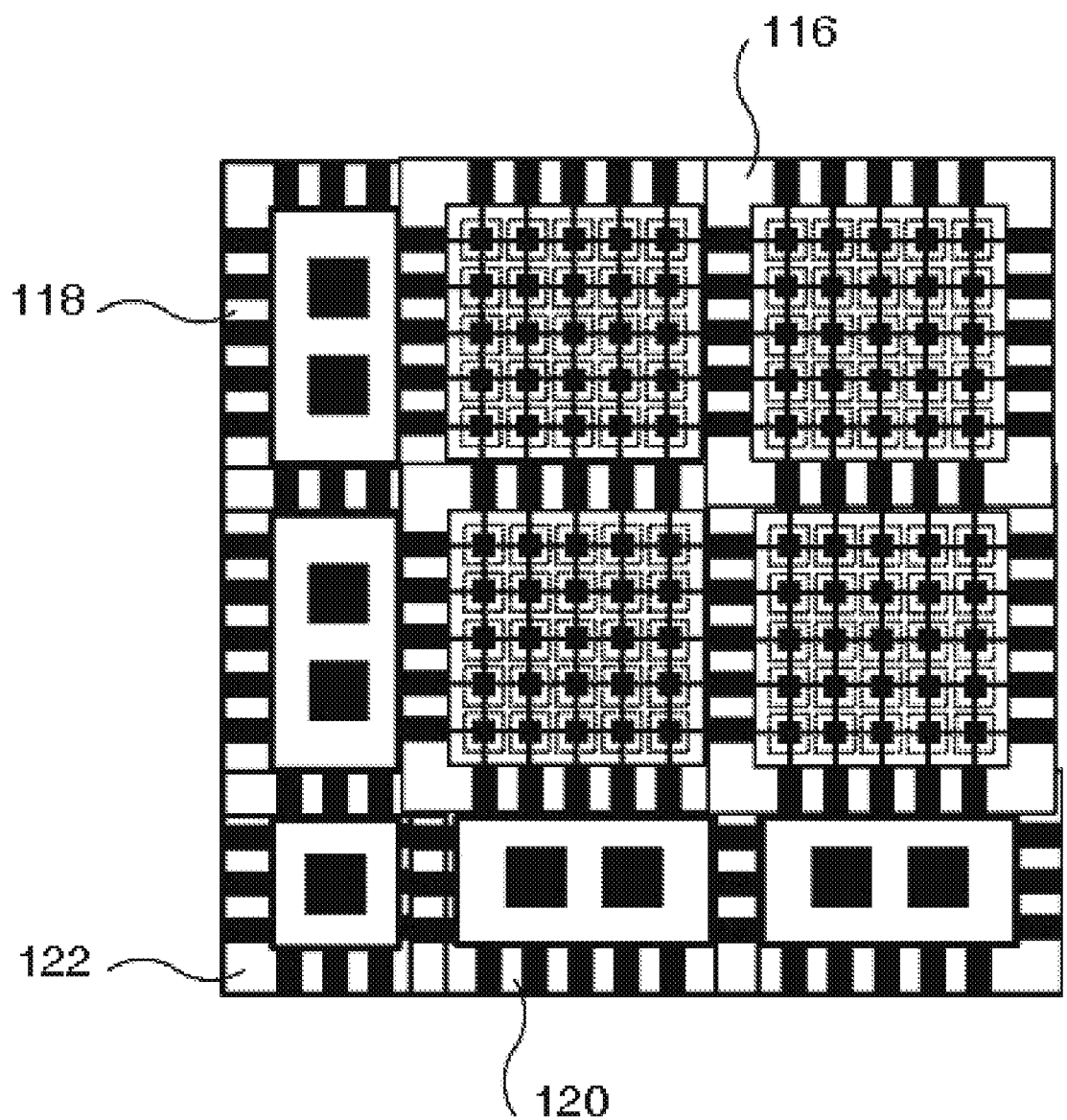
FIG. 2 is a high level diagram of a tactile system including four of the tactile sensor modules of FIG. 1B coupled together, two interface circuits of FIG. 1A coupled to the column edge conductor pads, two interface circuits of FIG. 1A coupled to the row edge conductor pads, and a control circuit coupled to two adjacent interface circuits.

FIG. 2 illustrates a second embodiment which includes expansion of the sensor system by attaching multiple modules. A sensor system can be formed by connecting multiple sensor modules and circuit modules electrically. Modules can be connected directly to each other, or connected using flexible connection modules that contain interconnection lines. The arrangement of modules is not limited to the arrangement shown in the FIG. 2 and can be changed as required.

Referring again to FIG. 2, sensor modules 116 are arranged to form a matrix. Circuit modules are placed on the edge of the sensor matrix. Circuit module 118 can select or address a specific row of the sensor matrix. Circuit module 120 can select a specific column and read out the sensor response. Circuit module 122 can control the other modules and transmit the measured signals to the outside. In some embodiments, each circuit module can include each function separately. In other embodiments, each module can include all functions, so that a proper function can be selected automatically by specific location or by a signal as required.

A third embodiment relates to implementing a sensor system on a single platform. All the functions of the second embodiment can be integrated in a single system of the third embodiment, if a sensor system of specific size and shape is required. The fabrication method and materials can be the same as with embodiment 2, except that the system is fabricated on a single substrate.

Figure 3:
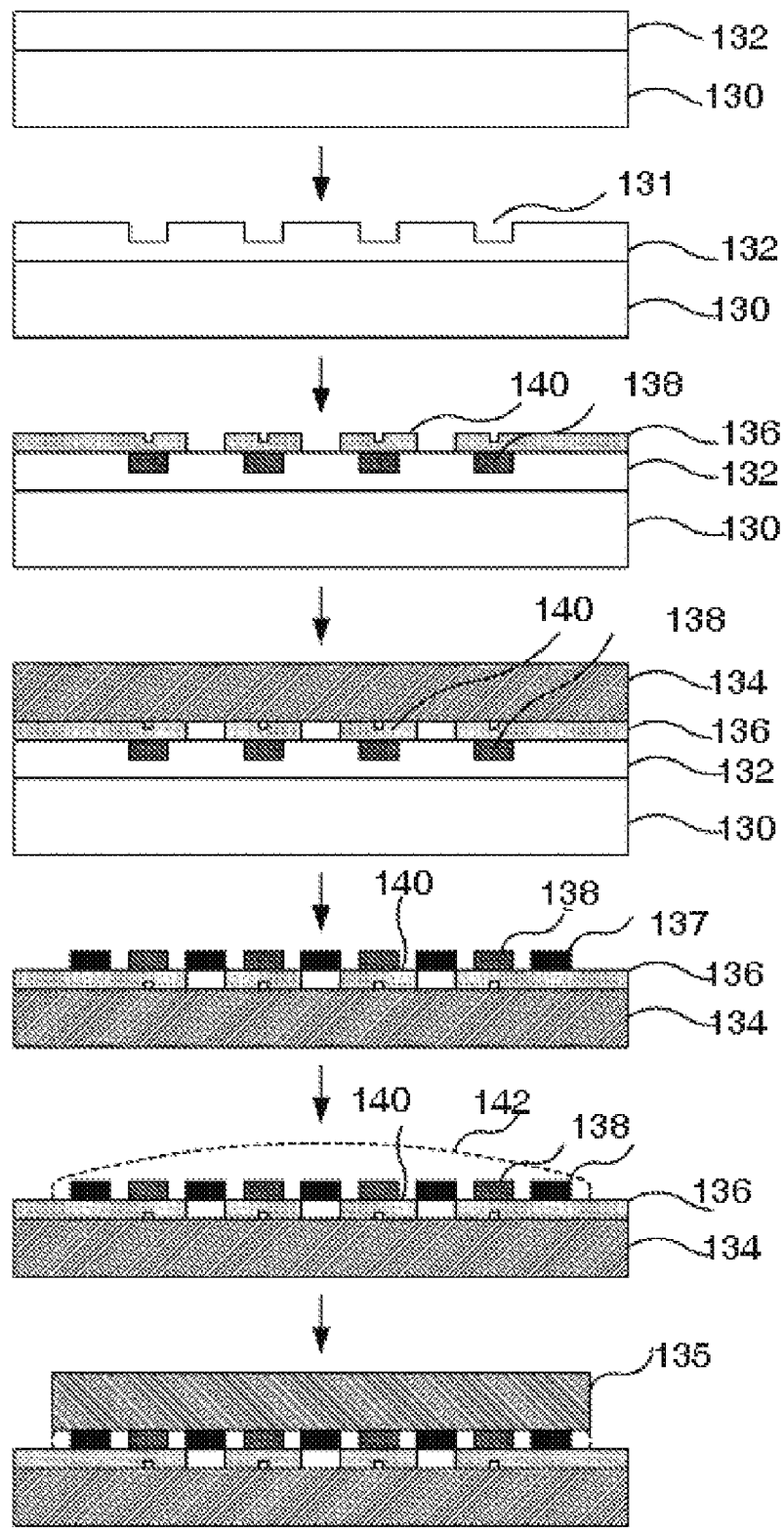
FIGS. 3 and 4 are process flow diagrams of a fabrication process of a circuit module and a sensor module.

FIG. 3 illustrates a fourth embodiment, a fabrication process of the circuit modules. According to FIG. 3, a sacrificial layer 132 is formed on a silicon wafer 130 first. Bump molds 131 are formed by etching part of sacrificial layer 132. Next, routing lines 140, interconnection lines 136, and bumps 138 are formed on the sacrificial layer by electroplating. Then, a polymer is spin coated and cured to form a substrate 134. By removing sacrificial layer 132, the substrate is detached from the silicon wafer 130. Next, an insulation polymer 137 is applied on the substrate 134 except on bumps and interconnection lines to prevent short circuits between routing lines and IC chips 135 that will be integrated. Finally, anisotropic conductive paste is applied where the IC chips 135 will be located and IC chips 135 are placed on bumps. Then, IC chips 135 are bonded to the substrate by applying pressure and heat.

Figure 4:
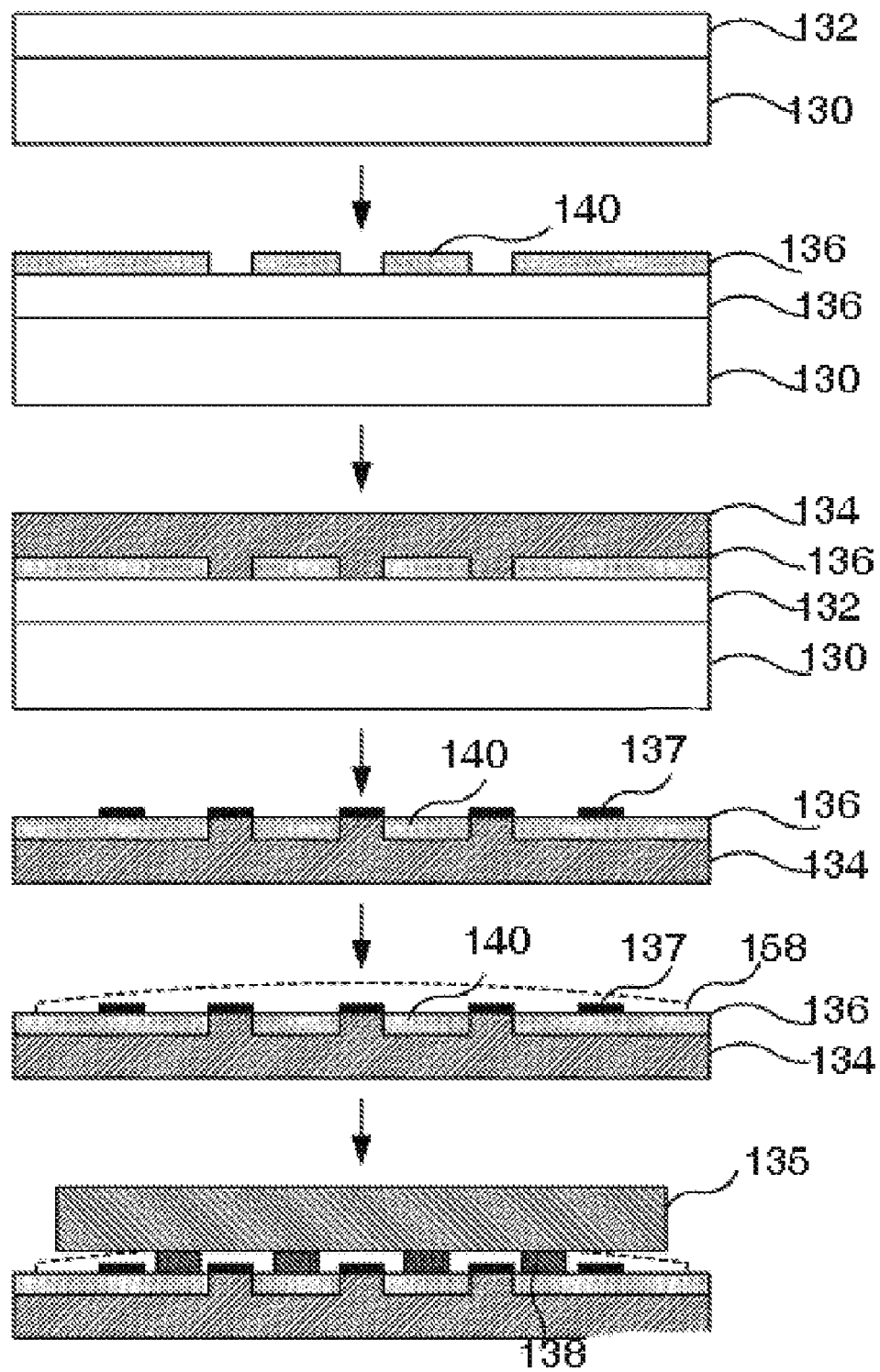

FIG. 4 illustrates a fifth embodiment, in which, during the fabrication of circuit modules, bumps can be placed on IC chips 135 instead of substrate 134. According to FIG. 4, a sacrificial layer 132 is formed on a silicon wafer 130 first. Next, routing lines 140 and interconnection lines 136 are formed on the sacrificial layer by electroplating. Then, a polymer is spin coated and cured to form a substrate 134. By removing sacrificial layer 132, the substrate is detached from the silicon wafer 130. Next, an insulation polymer 137 is applied on the substrate 134 except where bumps will be bonded and on interconnection lines to prevent short circuits between routing lines and IC chips 135 which will be integrated. Finally, anisotropic conductive paste is applied where the IC chips 135 will be located and IC chips 135 with bumps are placed. Then, IC chips 135 are bonded to the substrate by applying pressure and heat.

In another aspect, a sixth embodiment is related to fabricating sensor modules. All the processes can be the same as in the fourth and fifth embodiments, except that sensors are bonded to the substrate instead of IC chips.

Figure 5A:
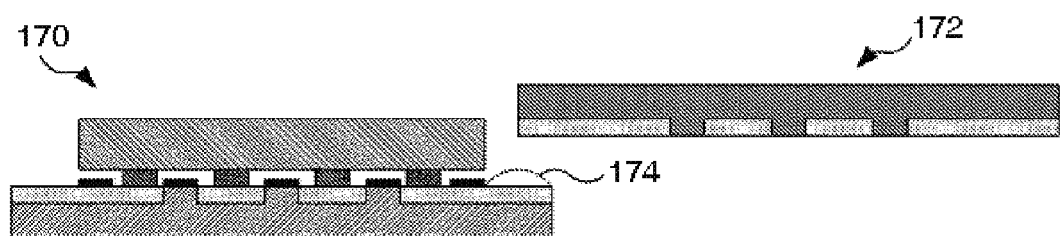
FIGS. 5A and 5B are schematic views of methods for joining modules together.
Figure 5B:
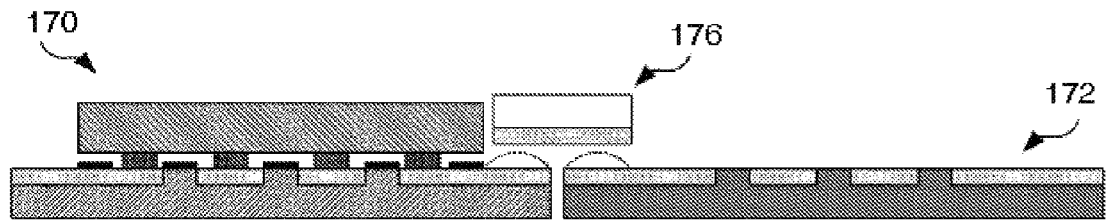

FIG. 5A illustrates a seventh embodiment, related to connecting circuit modules 170 and sensor modules 172. Circuit modules and sensor modules can be connected to each other through interconnection lines using anisotropic conductive paste (ACP) as shown in FIG. 5A. Extra connection modules 176 can be used to connect modules as shown in FIG. 5B.

Another aspect, an eighth embodiment, is related to fabricating a sensor system mentioned in the third embodiment. The fabrication process can be the same as that of the circuit modules except that both IC chips and sensors are bonded together on a single substrate.

Figure 6:
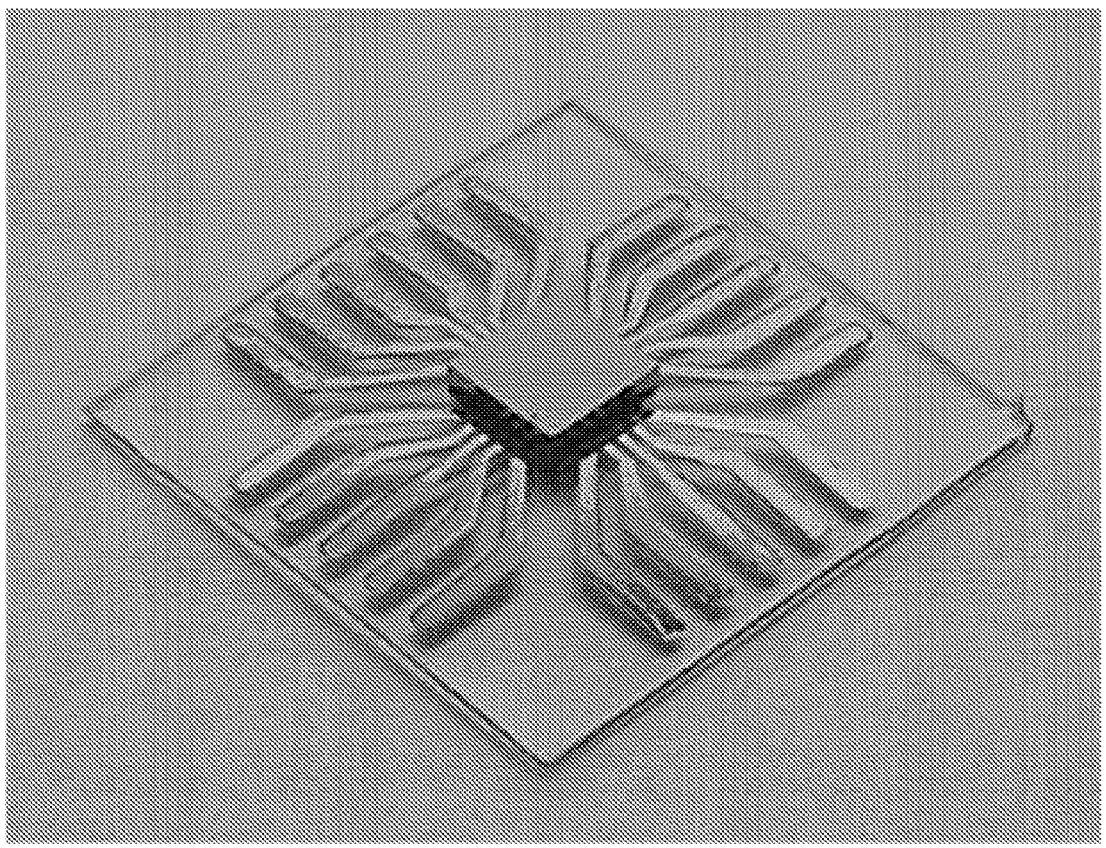
FIG. 6 is a photograph of a fabricated circuit module according to the present invention.

FIG. 6 is a photograph of a fabricated circuit module according to the present invention.

Figure 7:
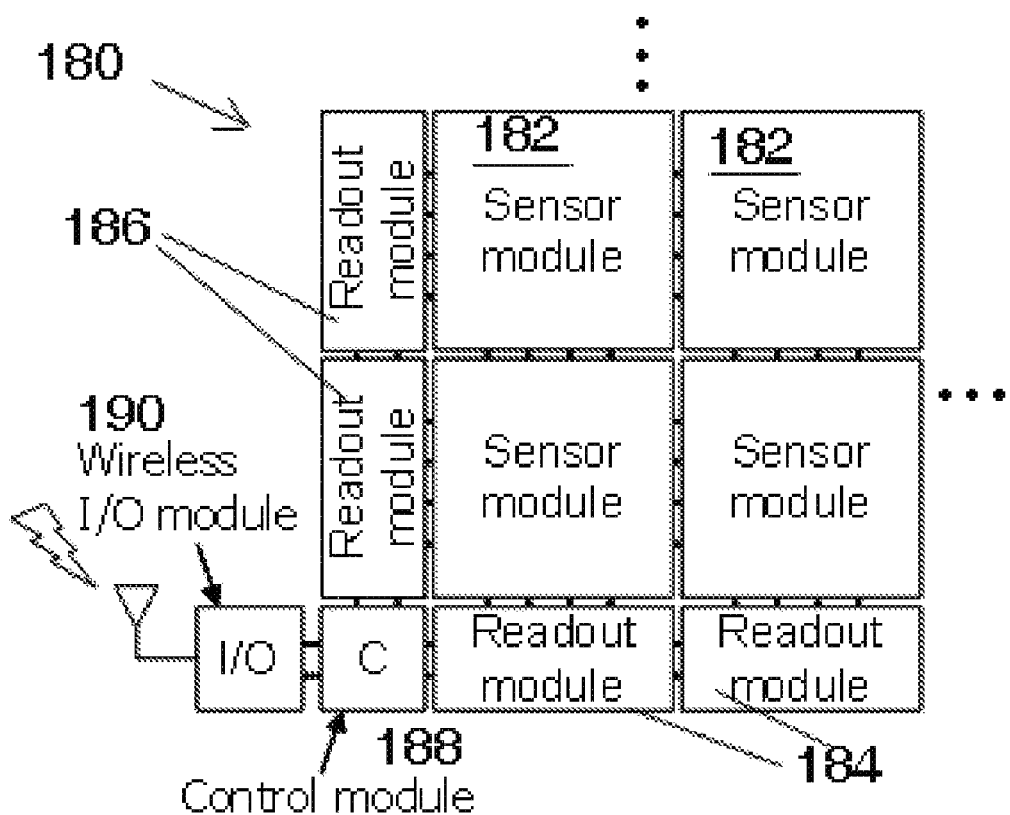
FIG. 7 is a schematic view of one modular expandable sensor system

FIG. 7 shows a schematic view of one expandable sensor system 180. In this figure, there are four basic modules: sensor modules 182, readout modules 184 and 186, a control module 188, and a wireless I/O module 190. In addition, other modules with different functions can be included if required. Information sensed by a sensor array in a sensor module is selected and can be converted to an electrical signal by a readout module and then transferred to the wireless I/O module. A wireless I/O module can transmit sensor data to an external base station and may receive control signals from it. A control module may manage these operations. As shown in FIG. 7, the sensor system can be expanded to a larger area by stitching more sensor modules and readout modules.

Figure 8:
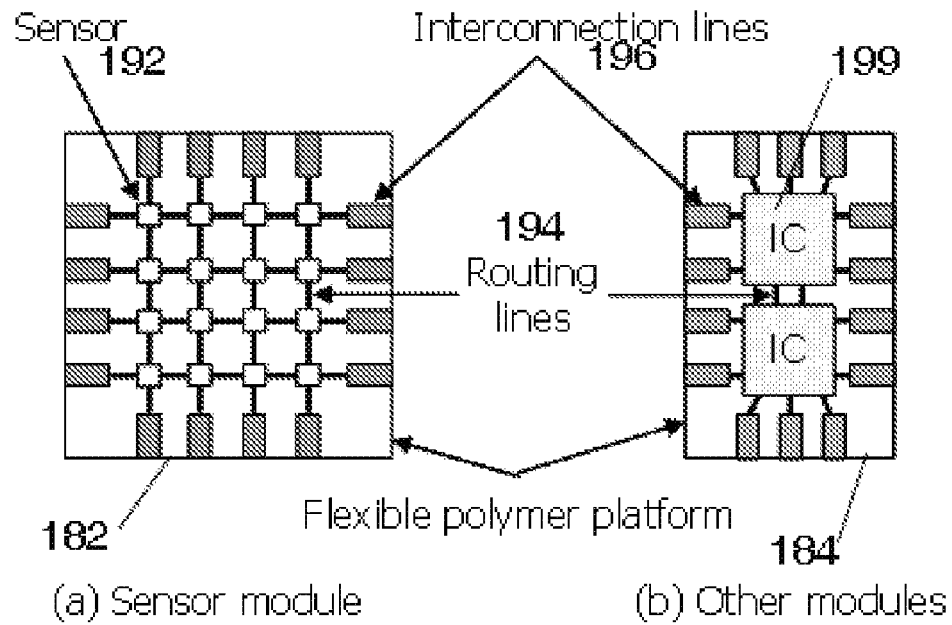
FIG. 8 is schematic diagram of a sensor module and other modules.

FIG. 8 shows a high level diagram of each module. Sensor modules 182 can include a sensor array and interconnection lines 196 on a flexible polymer platform. All of the sensors 192 may be connected to each other and to interconnection lines electrically through routing metal lines 194. Actually, interconnection lines 196 can be the edge part of the routing metal lines, and are also referred to as edge pads or edge conductors in some views of the invention. The edge conductors need not (but may) extend all the way to the edge, as the electrical bonding may be accomplished using overlap of adjacent modules or overlap of interconnection modules, in some embodiments. Routing lines 194 may be viewed as address and/or data lines in some views of some embodiments of the invention, and my serve both functions in some devices. All other modules including a readout, control, and wireless I/O module may have similar structures at a high level. They can include an IC (Integrated Circuit) 199 mounted on flexible polymer platform and interconnection lines. The integrated ICs can determine the basic functions of the module such as readout, control, wireless I/O or others. There can be routing metal lines on the platform which connect ICs and interconnection lines. Each module may be connected through interconnection lines electrically and mechanically by using Anisotropic Conductive Paste (ACP).

Figure 9:
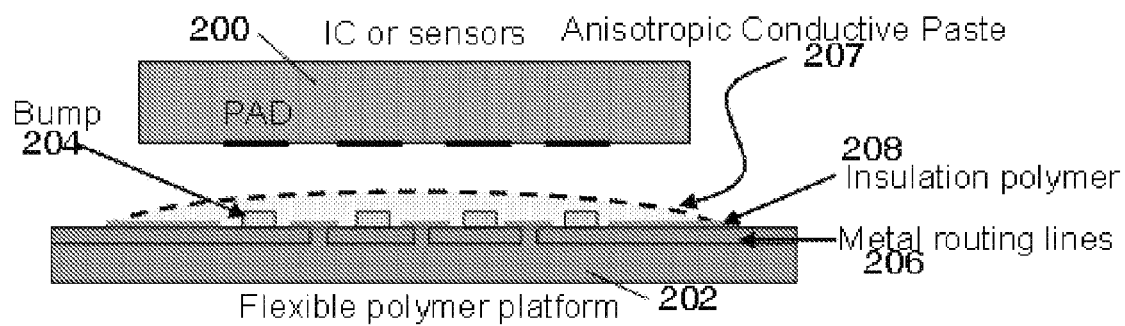
FIG. 9 is diagram of the integration of ICs or sensors on a flexible polymer platform.

FIG. 9 displays one way to integrate an IC or a sensor, both referenced as 200, on the flexible polymer platform 202. Basically, a polymer platform can include a polymer substrate 202, patterned routing metal lines 206, and an insulating polymer layer 208 for preventing a short circuit. Multi-level metal lines can be employed if required. ACP 207 can be used to integrate ICs or sensors on the platform. ACP is a kind of commercial adhesive which includes tiny electrically-conducting metal balls. Initially, it is insulating because the concentration of metal balls is too low for conduction.

However, once it is squeezed between metal pads (or bumps) and cured, ACP provides fairly good conduction through squeezed metal balls in a vertical direction as well as providing good mechanical bonding strength. ACP is cured with adequate pressure and heat for a short period of time. Bumps are often important structures for integration. Bumps can be formed either on the polymer platform or pads of an IC or a sensor. If a sensor is composed of polymer structure, it can be directly implemented on the platform during the platform process instead of being bonded by using ACP.

Figure 10:
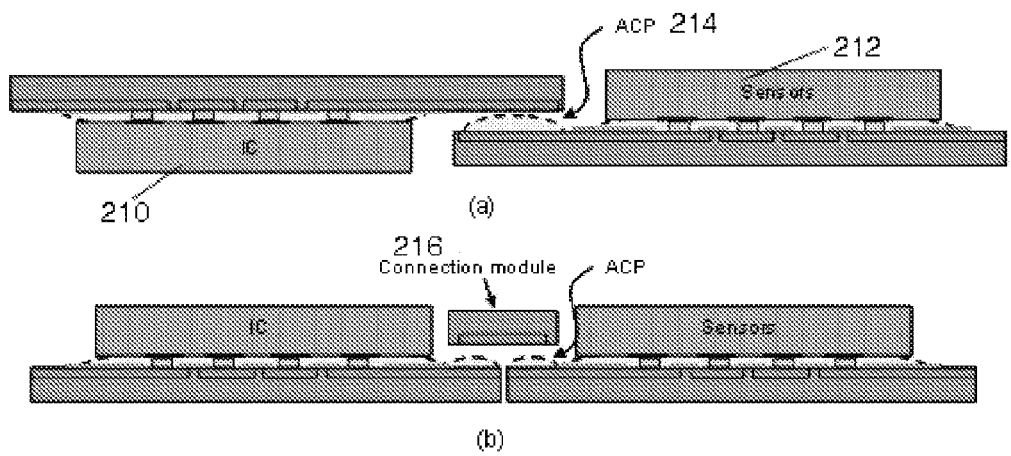
FIG. 10 is a diagram of two module bonding methods.

FIG. 10 illustrates some module bonding methods. ACP can also be used for module bonding. Modules may be attached directly or by using a connection module as shown. If we attach modules directly, sensors 212 and ICs 210 will see the opposite direction. If we use a connection module 216 as in FIG. 10(b), sensors and ICs can be placed on the polymer platform facing the same direction.

This invention can provide a flexible sensor system to which a modular concept is introduced to make the system expandable. This invention can provide a common flexible platform for sensor systems for artificial tactile skin for robots, and flexible bio-monitoring systems in smart clothes, and wearable computers. This can provide a modular concept to make a sensor system expandable to any size. This invention can also provide a simple method to attach modules and integrate ICs or sensors by using commercial ACP on a flexible polymer platform such as a silicone rubber.

Figure 11:
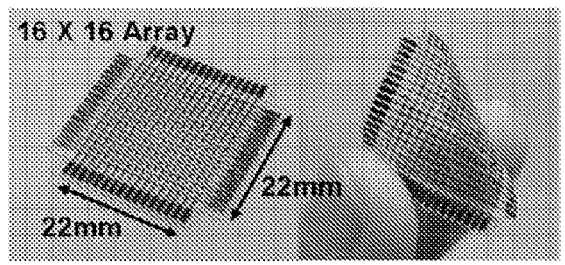
FIG. 11 includes two photographs of a tactile sensor module.

FIG. 11 shows a prototype of a capacitive tactile sensor. The sensor is composed of a 16×16 cell array, with a spatial resolution of 1 mm and having a contact resistance less than 0.1 ohms using ACP. A flip chip assembly process using ACP was used to accommodate all the readout circuits on a soft polymer substrate.

Figure 12:
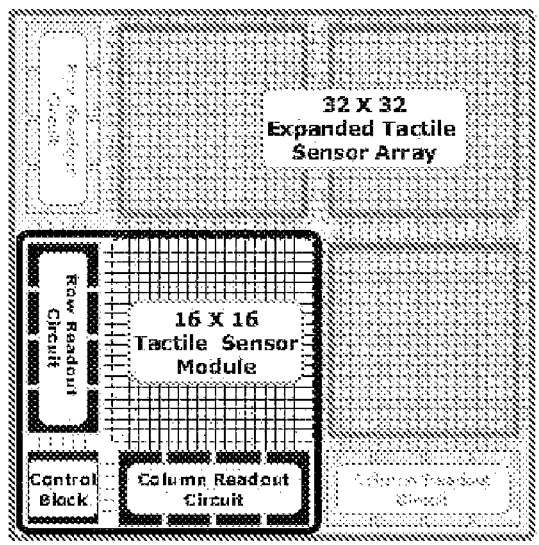
FIG. 12 is a diagram of a modular expandable tactile sensor scheme.

FIG. 12 illustrates a diagram of a modular expandable tactile sensing scheme. The proposed tactile sensor system consists of four components: 16×16 sensor array modules, row and column readout circuits, and a control block. Each array sensor module and readout circuit module can be separately fabricated. To form the expanded integrated tactile sensing system, each module can be assembled and electrically connected through metal interconnections on soft polymer substrate. As an example, an expanded 32×32 array sensor system is shown in FIG. 12.

Figure 13:
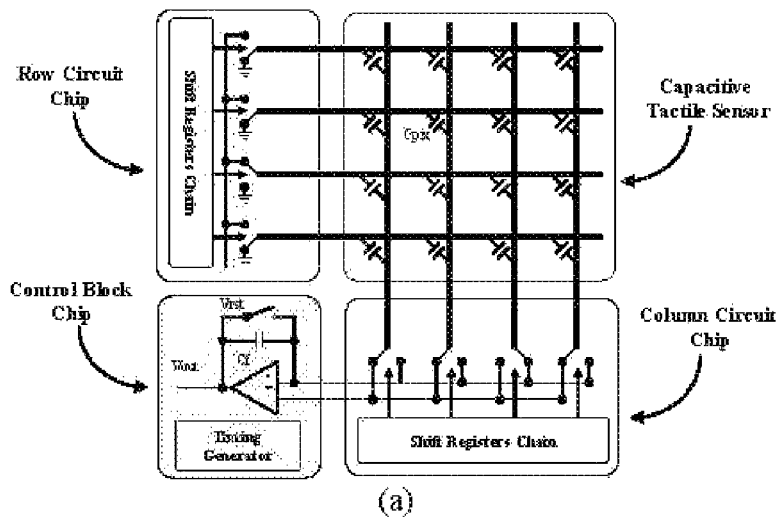
FIG. 13 is a schematic diagram of a modular expandable readout circuit scheme and a timing diagram.
Figure 13:
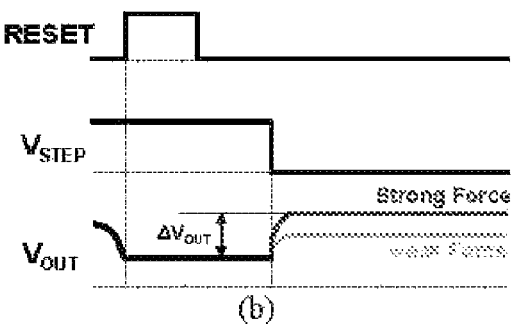

FIG. 13 shows a schematic diagram of a modular expandable readout circuit scheme. For simplicity, a 4×4 array sensor is shown with row/column circuit chips and a control block chip. Capacitance of each taxel (tactile cell) is measured by a simple charge amplifier. The initial capacitance of a taxel has been measured as 180 fF. The readout procedure can be as follows. First, each taxel is selected by row and column shift registers and a reset signal is applied in order to reset the amplifier. Then, a step-function signal is applied to the target capacitor and the stored charge $C_{pix}$ during the reset phase is transferred to the feedback capacitance $C_f$ which generates output voltage by a charge amplifier in the control block. The output voltage variation, $\Delta V_{out}$, becomes $$\Delta V_{out} = -\Delta V_{step} \times (C_{pix}/C_f) [V]$$

Where $C_{pix}$ is the cell capacitance in the array, $C_f$ is the feedback capacitance of the charge amplifier, and $\Delta V_{step}$ is the applied step voltage to $C_{pix}$. $V_{out}$ is determined by the capacitance of $C_{pix}$ which is changed by the applied force onto a taxel. When a strong force is applied, capacitance $C_{pix}$ becomes larger. All this operation can be controlled by the timing generator in the control block. In order to extend the sensor array, simply more chips are added to the end of the column and/or row of the existing sensor array. However, it is cumbersome and expensive to fabricate three different types of ID chips for each different function such as the row/column decoders and the control block with a timing generator.

Figure 14:
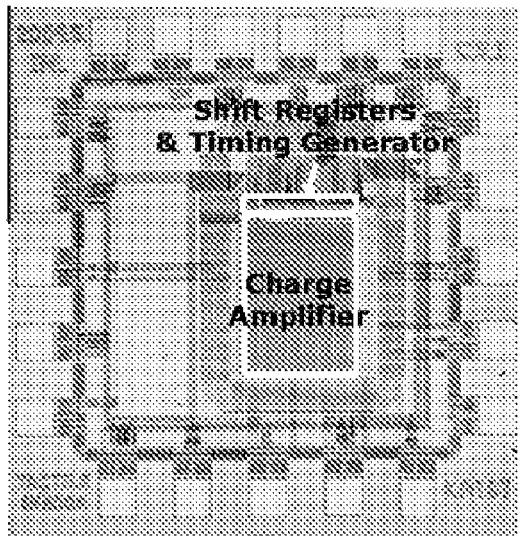
FIG. 14 is photograph of a fabricated universal readout circuit chip.

To overcome this obstacle, we have devised a universal chip in which all three circuit blocks are realized. A specific block function in the universal generic chip can be automatically self-configured by its position and neighboring ships in the system. The micrograph and characteristics of the finishes readout circuit are show in FIG. 14 and Table 1, respectively.

TABLE 1

| Characteristics of the chip | |
|---|---|
| Technology | 0.35 micrometer 2 poly 3 metal Standard CMOS |
| Chip Size | 2 mm × 2 mm |
| Supply Voltage | 3.3 V |
| Frame Rate | 24 frames/s (@16 × 16 Array Size) |
| Power | 551.1 microW 9@control Block) 13.3 microW 9@Column/Row) |

Figure 15:
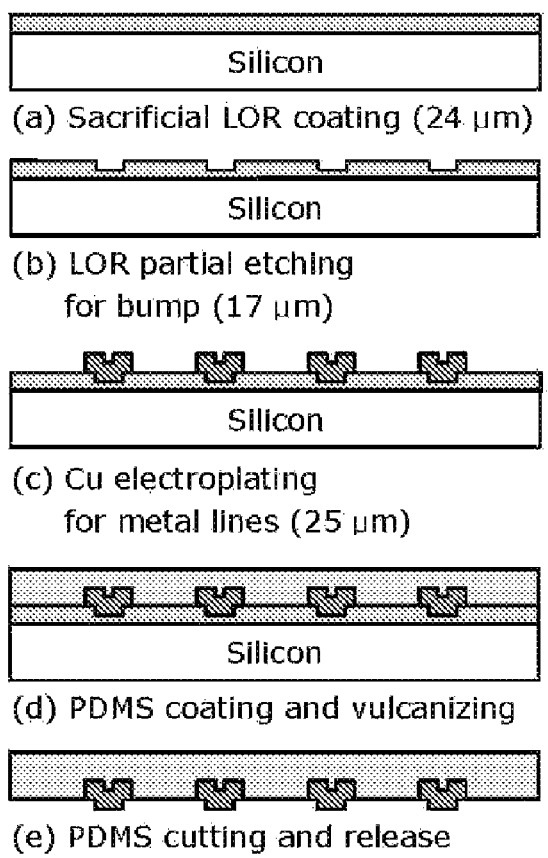
FIG. 15 is an illustrated process diagram of a fabrication process using a polymer substrate as a platform for readout circuitry modules.

FIG. 15 illustrates a fabrication process of a polymer substrate platform for readout circuitry modules with embedded interconnection. The structure and material of the platform can be similar to those of the modular array sensor, except for small metal bumps on the embedded interconnection lines for assembly with IC chips.

Fabrication processes can be as follows. First LOR (Lift-Off-Resists) from Microchem is spin coated by 24 micrometers on a bare silicon wafer as a sacrificial layer. Then it is partially etched by 17 micrometers in AZ400K developer to form a mold for metal bumps by a plasma etcher. Copper lines and bumps for flip-chip bonding are simultaneously formed using electroplating. Bump size is 100 micrometers by 100 micrometers. Next, titanium is sputtered as an adhesion layer and PDMS is spin-coated at 300 micrometers. This PDMS layer should be cured at room temperature to prevent the layers from being deformed after release due to thermal expansion difference between the copper and PDMS layers. Also, they should be cured on a custom designed planarization stage to get uniform thickness. Thickness variation can be controlled under 20 micrometers over a 4 inch wafer. After vulcanizing the PDMS, the platform layer is cut and released from the carrier wafer.

Figure 16:
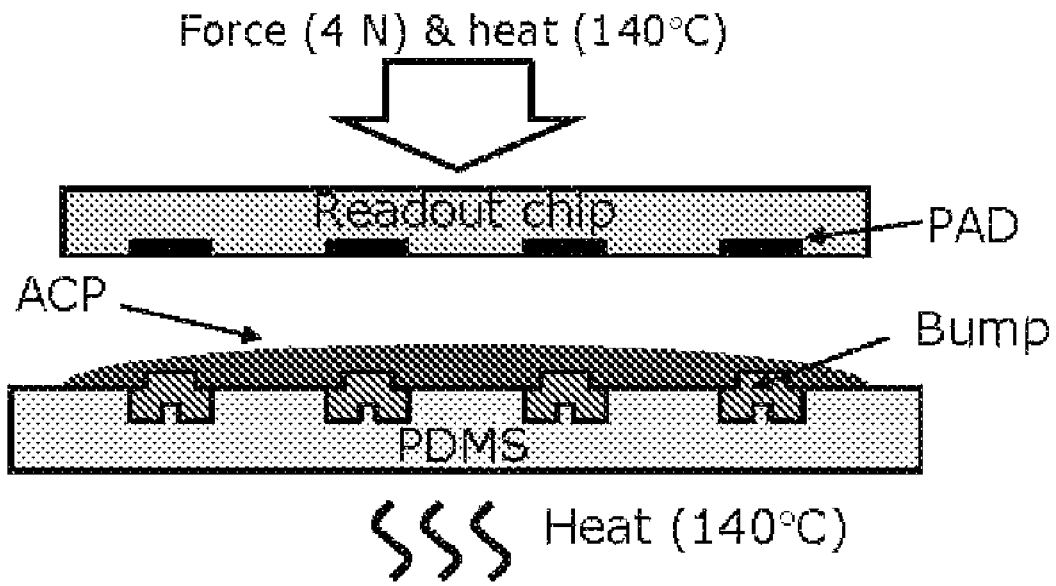
FIG. 16 is an illustrated process diagram of a flip chip assembly process using ACP.
Figure 16:
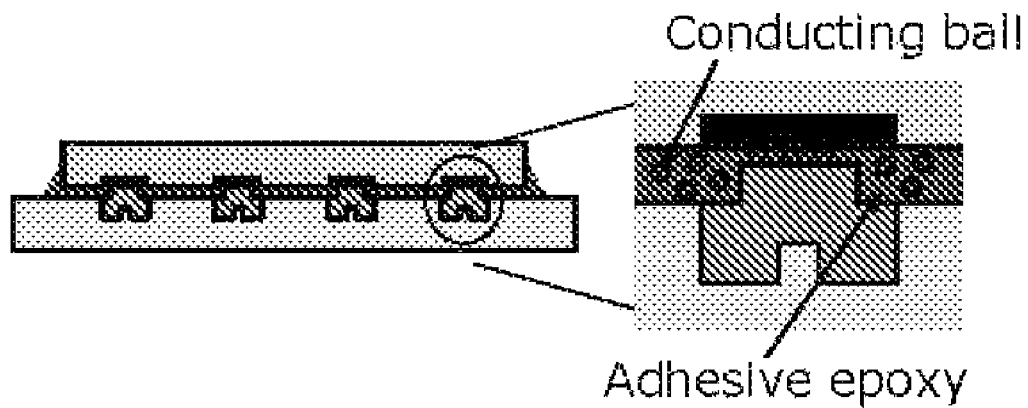

FIG. 16 illustrates the hybrid integration of readout circuit chips on soft polymer substrate platform demonstrated by the flip-chip assembly process shown, using anisotropic conductive paste (ACP) which is widely used in PDP or LCD packaging. ACP is a kind of thermally curable epoxy adhesive including conducting balls. Once the ACP is squeezed between two electrodes and cured, the electrodes are connected electrically through the squeezed balls. To cure ACP, pressure of about 0.2 N per each bump has been applied at 140 degrees C. for 5 minutes as shown in FIG. 16(a). All the bumps on the platform and all the pads in the readout circuit chips were electrically connected without failure, with contact resistance below 100 mOhms. Mechanical bonding strength is so strong that the assembled chip could not be detached from the platform without tearing.

Figure 17:
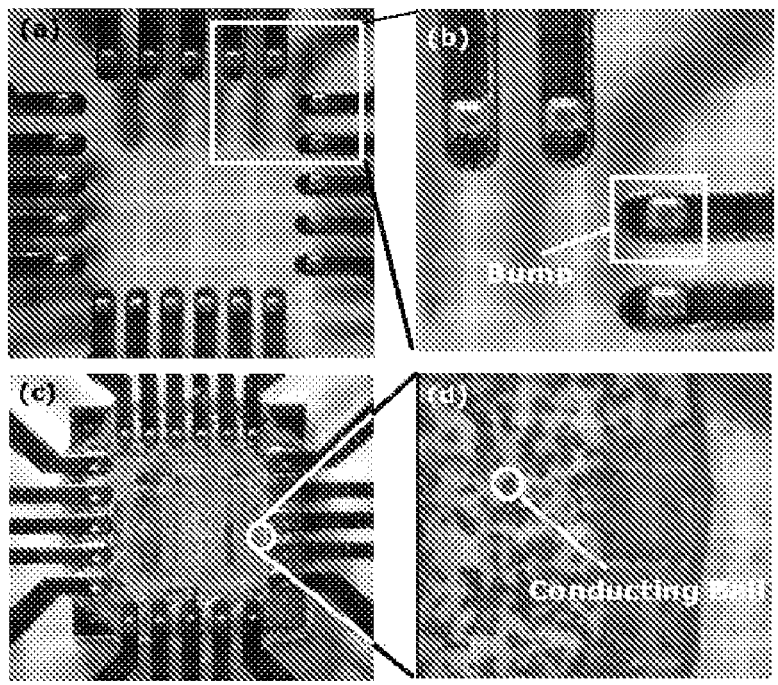
FIG. 17 is a group of four photographs of the fabricated PDMS substrate and the assembled chip on it.

FIG. 17 shows the fabricated PDMS substrate and the assembled chip on it. Photographs of the fabricated polymer substrate with metal lines and bumps, as well as a photograph of a flip-bonded chip (the backside) are illustrated along with a magnified view of ACP and the conducting balls.

Figure 18:
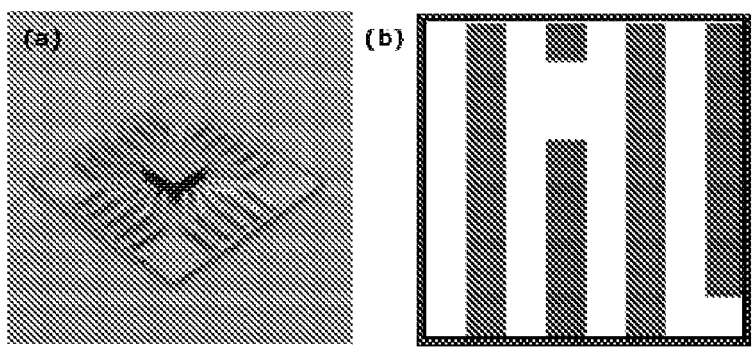
FIG. 18 is a photograph of the flip chip bonded on polymer substrate and an image captured from a tactile sensor using the sensor array with readout circuit chips.

FIG. 18 shows how the assembled chip was attached to the PCB and tested. The chip was flip bonded on polymer substrate in FIG. 18(a). All the pads were successfully connected to the substrate. FIG. 18(b) shows a captured 8×8 image of the letters 'IML' from the fabricated tactile sensor array assembled with readout circuit chips on a test board.

EXAMPLES OF SENSOR MODULES

Figure 19:
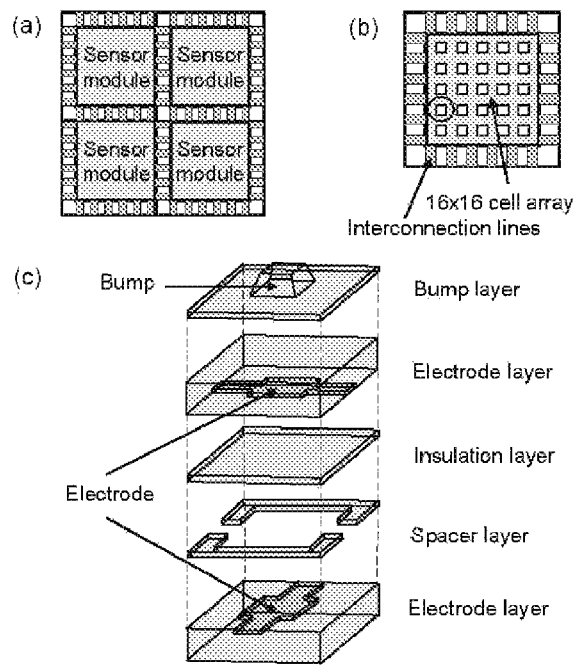
FIG. 19 is schematic view of a modular expandable tactile sensor.

FIG. 19 illustrates one modular expandable tactile sensor according to the present invention. Each sensor module can be connected through interconnection lines to form a larger sensor skin. One sensor module consists of a 16×16 cell array and interconnection lines. The spatial resolution is 1 mm which is similar to that of human skin. The cell is composed of five PDMS layers and copper electrodes sandwiched between PDMS layers.

Figure 20:
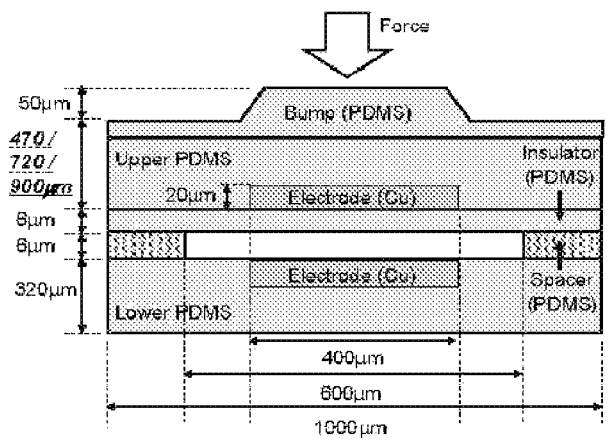
FIG. 20 is cross-sectional view of a tactile cell with dimensions.

FIG. 20 shows the cross-section of the proposed cell and its dimensions. Two electrodes form a capacitor separated by 6 micrometers via a spacer. The cell and electrode size are 600×600 micrometers and 400×400 micrometers, respectively. Initial capacitance of one cell has been estimated as 171 fF assuming the relative permittivity of PDMS as 2.75 from the product manual (Sylgard 184, Dow Corning). When pressure is applied to a bump, the upper PDMS deforms and the capacitance increases until the gap is closed. The thickness of the upper electrode layer and bump layer determines the sensitivity. Three cells with different PDMS thicknesses, 470, 720, and 900 micrometers, have been tested.

Figure 21:
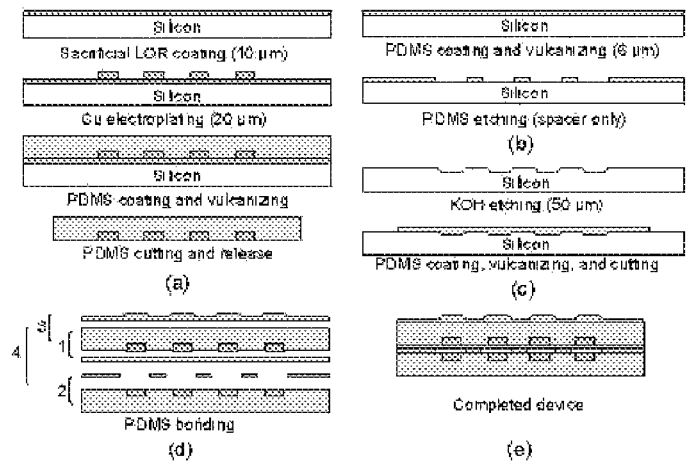
FIG. 21 is an illustrated process diagram of a fabrication process for a tactile sensor module.

FIG. 21 illustrates a fabrication process of a sensor module. Each layer can be processed separately and bonded together after oxygen plasma treatment. For the electrode layers, LOR from Micro-chem is spin coated about 10 micrometers on a bare silicon wafer. LOR is used as a sacrificial layer. The copper electrode (20 micrometers) is formed using electroplating. Next, titanium is sputtered as an adhesion layer and PDMS is spin coated about 320 micrometers. PDMS should be cured at room temperature to prevent the layers from being deformed after release due to thermal expansion difference between the copper and PDMS layers. Also, they should be cured on a custom designed planarization stage to get uniform thickness. Thickness variation can be controlled under 20 micrometers over a 4 inch wafer. After vulcanization the PDMS at room temperature, the electrode layer is cut and peeled off. The insulation and spacer layers are formed by spin coating PDMS diluted with hexane on bare silicon wafers with sputtered platinum. Platinum has been used to weaken PDMS adhesion to the substrate. The thickness of both layers is 6 micrometers. Then, PDMS is patterned and etched in a RIE with 3:1 $SF_6/O_2$ gas to form a spacer layer. The bump is formed using a silicon wafer etched in KOH as a mold. Five layers are aligned and bonded together using a conventional contact aligner with slight modification. The total thickness of the cells has been controlled by bump layer thickness.

Figure 22:
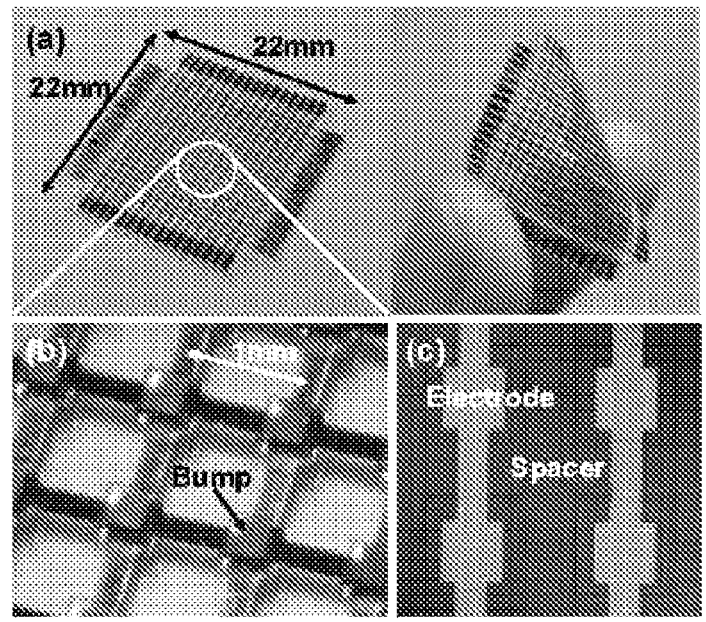
FIG. 22 is a group of four photographs of the fabricated sensor module.

FIG. 22 shows the fabricated tactile sensor module. The size of one sensor module is 22×22 mm including interconnection lines. The fabricated sensor shows flexibility, a seen in the photograph. FIG. 22($b$) shows the magnified view of four cells and FIG. 22($c$) shows the embedded electrode with a bonded spacer. Air channels are formed to prevent the squeezed air from affecting the cell response. These air channels connect all the cell cavities to atmosphere and maintain the pressure of each tactile cells cavity to the pressure of atmosphere. In other embodiments, the tactile cells cavities are in fluid communication with the atmosphere.

Figure 23:
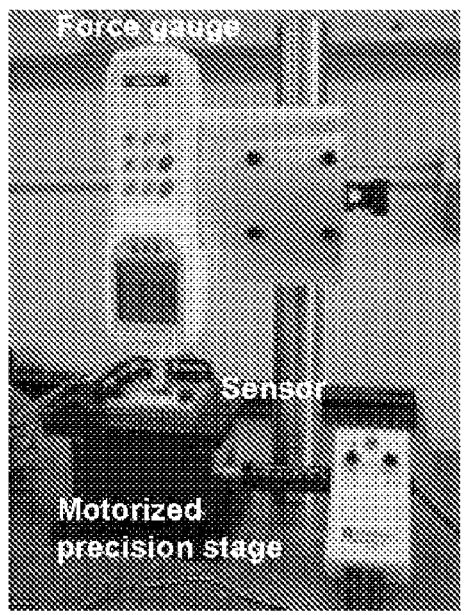
FIG. 23 is a photograph of a measurement setup for testing the sensor module.

FIG. 23 shows a setup for cell measurement. A micro-force gauge with 1 mN resolution has been used with a precision motorized translation stage with 100 nm resolution.

Figure 24:
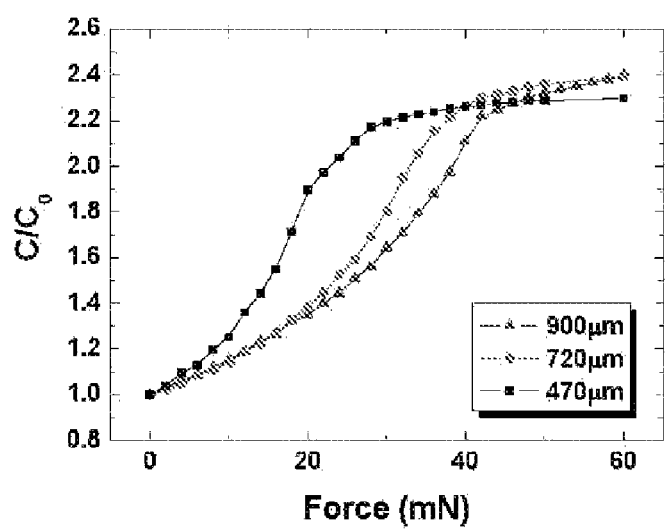
FIG. 24 is a plot of capacitance ratio vs. applied force for a sensor module.

FIG. 24 shows the measured response of the fabricated cells for various thicknesses of the upper PDMS layer. The Y axis represents the ratio of measured capacitance to initial capacitance as a function of applied force. The initial capacitance of a cell has been measured as 180 fF. Every cell shoes saturation after 40 nM (250 kPa), which means both upper and lower electrodes are in contact with an insulation layer in between them. The cell becomes more sensitive as the upper PDMS layer thickness reduces. A sensitivity of 3%/mN for a 470 micrometer thick membrane for a small deflection has been measured.

Figure 25:
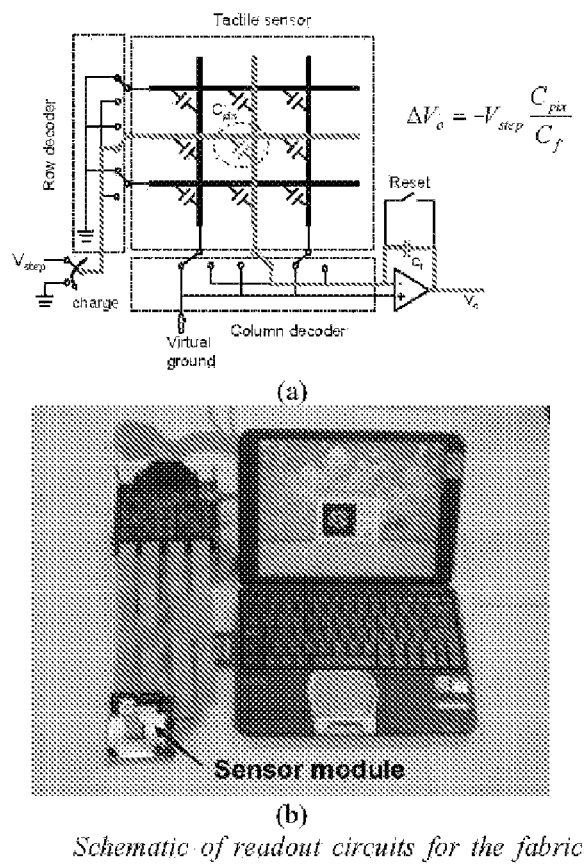
FIG. 25 is schematic of a readout circuit and a photograph of a sensor module test setup utilizing a computer display.

FIG. 25($a$) shows the schematic of readout circuits used to capture tactile images. FIG. 25($b$) shows the system setup for image capture. Each tactile cell is selected by a row decoder and reset first. Then it is charged to $V_{step}$. When it is selected by the column decoder the stored charge is transferred to feedback capacitance ($C_f$) and generates output voltage as described in the figure.

Figure 26:
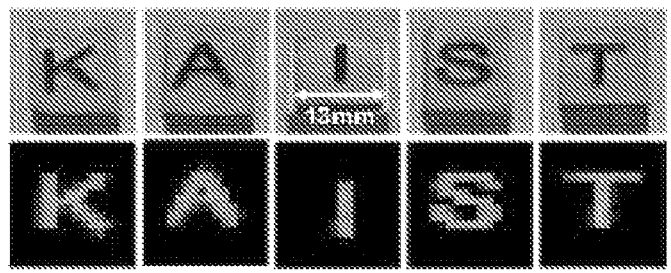
FIG. 26 is group of photographs of rubber stamp letters and the corresponding tactile sensor captured images.

FIG. 26 shows the captured images. Pressure has been applied using rubber stamps with an alphabet letter on them, and the corresponding images have been captured clearly.

Figure 27:
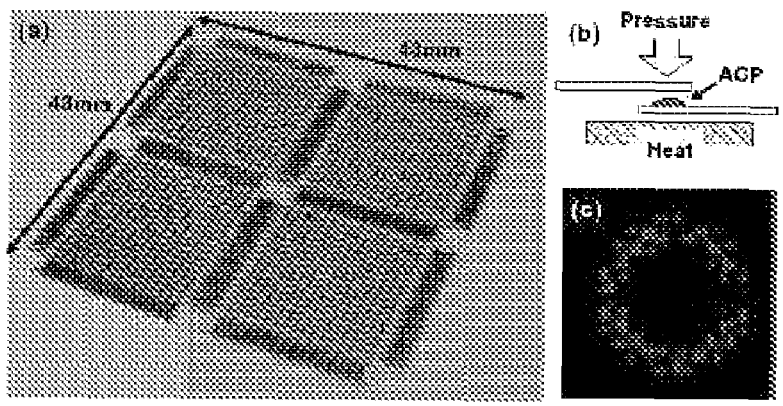
FIG. 27 is a photograph and a diagram of the expanded tactile sensor module, one bonding process, and a captured image.

FIG. 27($a$) shows the expandability of the sensor array in four sensor modules 'stitched' together. Anistropic Conductive Paste (ACP) was used, which is also used in PDP and LCD packaging. To cure ACP, pressure of about 0.4 MPa has been applied at 120 degrees C. for 15 minutes, as shown in FIG. 27($b$). All interconnection lines were electrically connected without failure with contact resistance below 100 mOhms. FIG. 27($c$) shows the tactile image of the letter 'O' captured by the expanded 2×2 sensor module array (a total 32×32 tactile cell array).

Figure 28A:
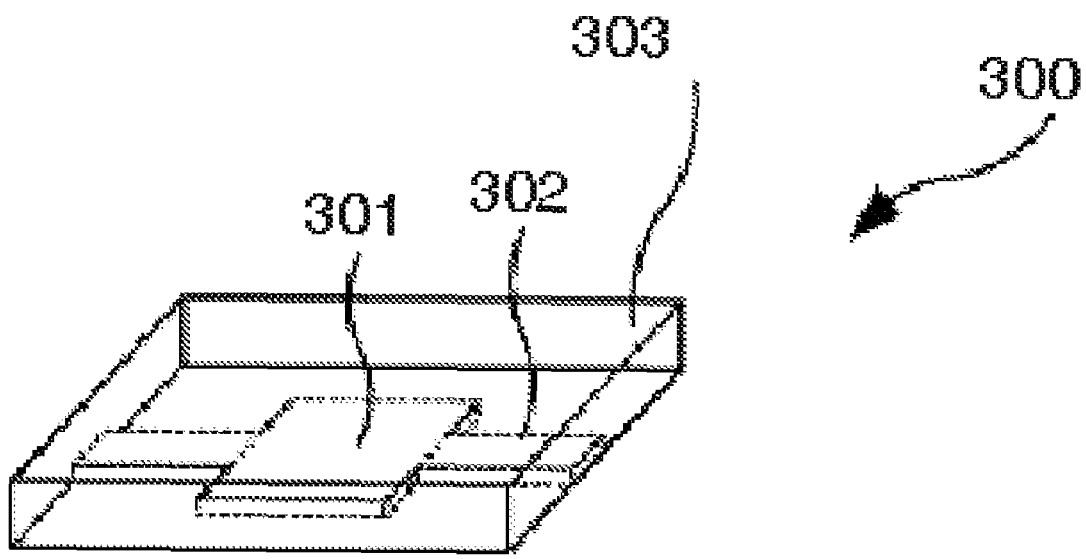
FIG. 28A is a perspective view schematically illustrating an electrode layer for capacitors according to a preferred embodiment of the present invention.

FIG. 28A shows an electrode layer 300 according to one embodiment of the present invention, comprising a substrate 303, an electrode 302, and a signal transmission line 302. The substrate 302 is made of flexible polymer, such as silicon-based rubber or polyimide.

The electrode 301 and the signal transmission line 302 are formed on the substrate 303. The signal transmission line 302 is connected to the electrode 301. Consequently, a signal generated by the change in capacitance of a capacitor, in which the electrode layer 300 according to this embodiment is used, is transmitted to the outside though the signal transmission line 302, which may be referred to as a data transmission line. The 'data", as the term is used herein, may be any signal indicative of a physical property, including variations in voltage, current, charge, continuously variable changes, discrete (on/off) changes, digital, binary, and the like.

Figure 28B:
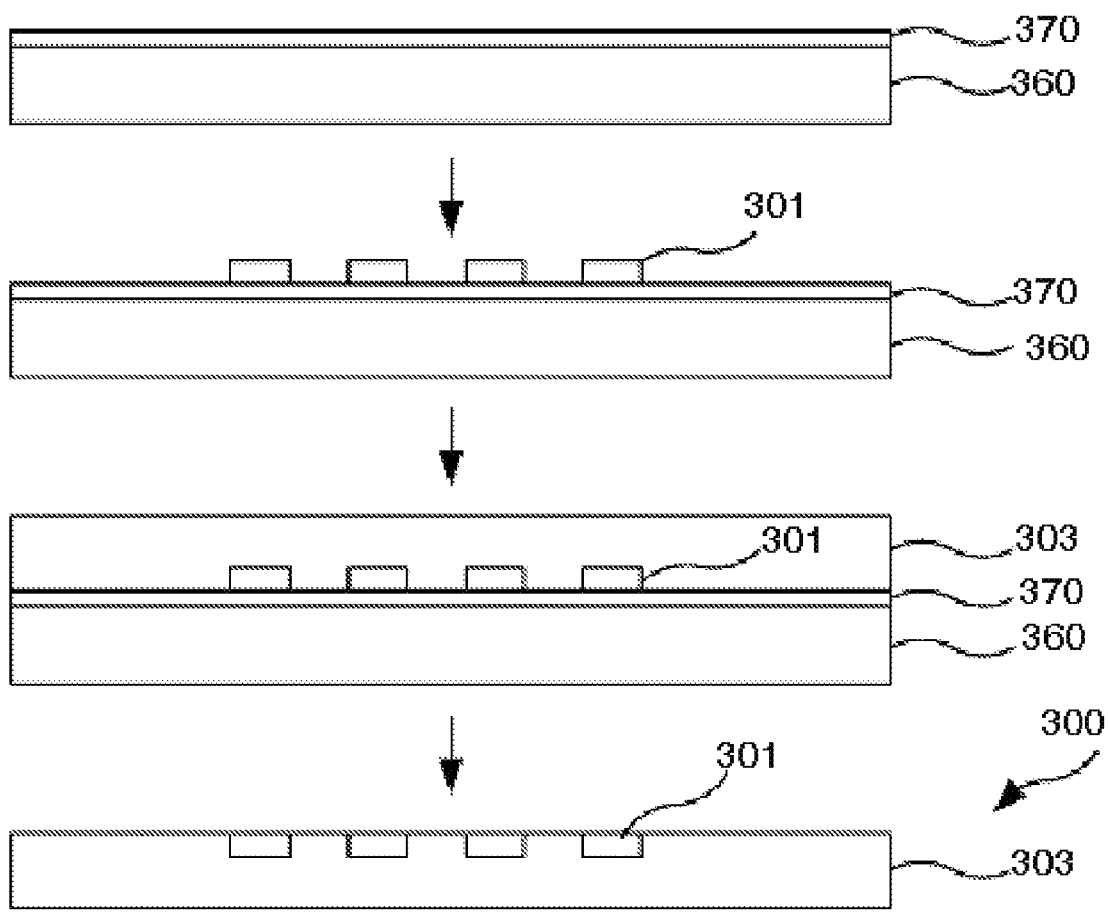
FIG. 28B is a sectional view schematically illustrating a method of manufacturing the electrode layer for capacitors shown in FIG. 28A.

FIG. 28B illustrates a method of manufacturing the electrode layer 300. A sacrifice layer 370 is formed on a silicon substrate 360. Next, a predetermined area on the sacrifice layer 370 is electroplated with a conductive material, such as copper or gold, to form an electrode 301 and a signal transmission line. Subsequently, the sacrifice layer 370, on which the electrode 301 and the signal transmission line are formed, is coated with liquid-state polymer, and then the liquid-state polymer is hardened, to form a substrate 303. Finally, the silicon substrate 360 and the sacrifice layer 370 are removed to manufacture an electrode layer 300, which comprises the substrate 303, the electrode 301, and the signal transmission line 302.

Using the electrode layer according to the first embodiment of the present invention allows a very flexible capacitor array to be manufactured.

Another embodiment of the present invention relates to a unit sensor using the electrode layer according to the first embodiment of the present invention as described in detail above.

Figure 29A:
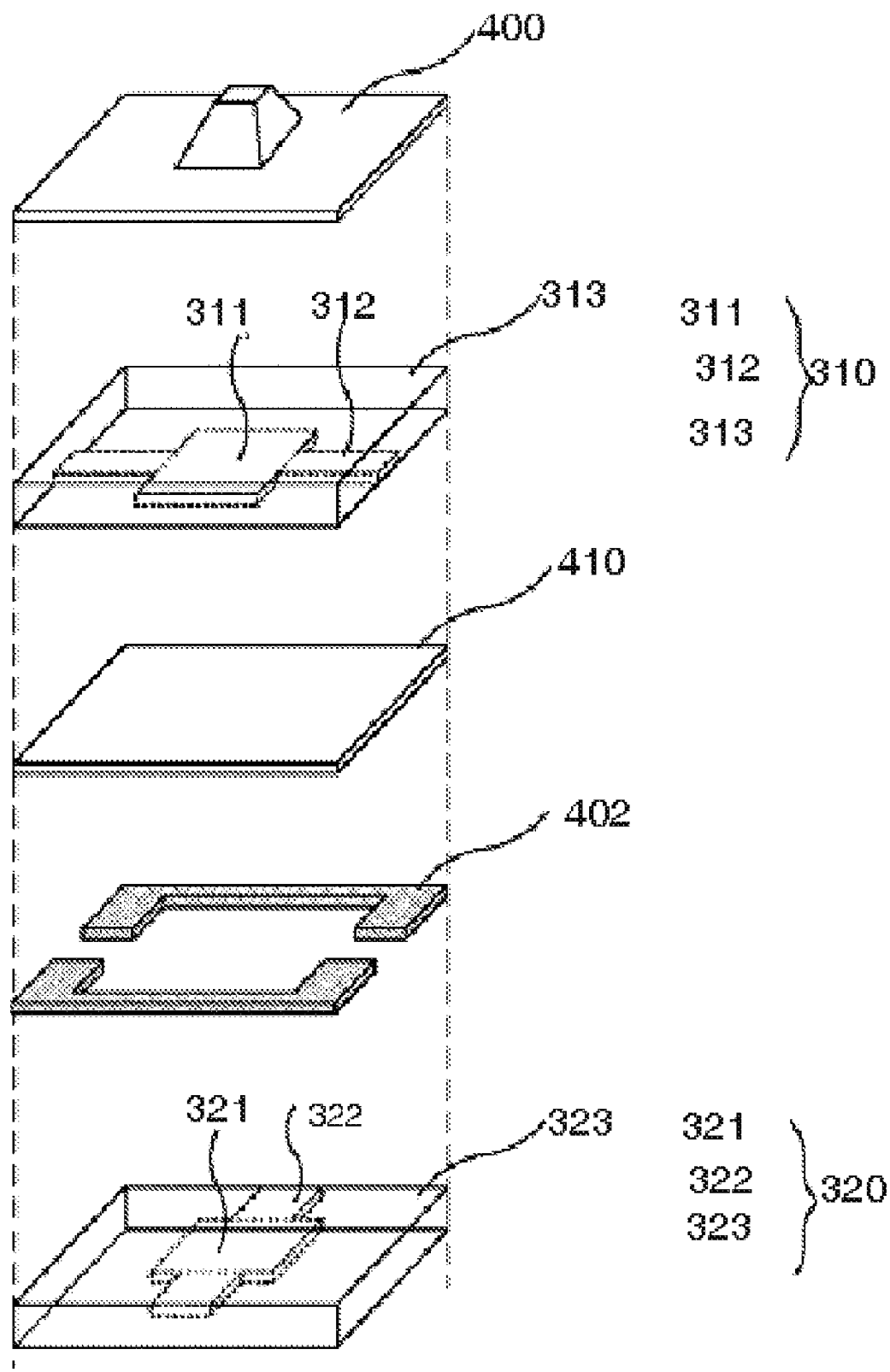
FIGS. 29A and 29B are an exploded perspective view, and a sectional view, schematically illustrating a unit sensor using the electrode layer for capacitors shown in FIG. 28A.
Figure 29B:
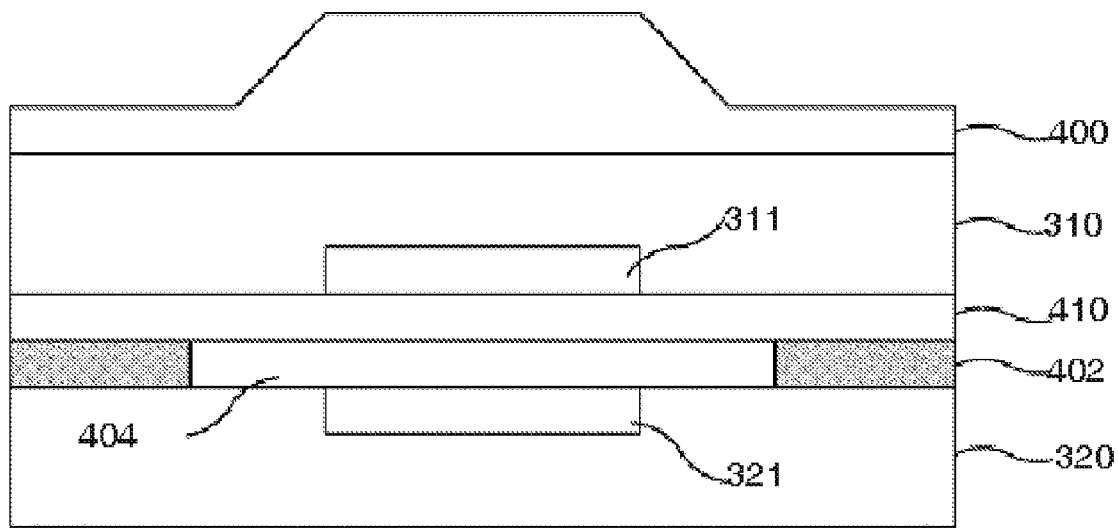

FIGS. 29A and 29B show a unit sensor according to another embodiment of the present invention comprises a lower electrode layer 320, a spacer layer 402 stacked on the lower electrode layer 320, an insulating layer 410 stacked on the spacer layer 402, an upper electrode layer 310 stacked on the insulating layer 410, and a bump layer 400 stacked on the upper electrode layer 310.

The upper electrode layer 310 comprises an upper electrode 311, a signal transmission line 312, and a polymer substrate 313. The lower electrode layer 320 comprises a lower electrode 321, a signal transmission line 322, and a polymer substrate 323. The upper electrode layer 310 and the lower electrode layer 320 are identical to the electrode layer 300 according to the first embodiment of the present invention as described in detail, and therefore, a detailed description of the upper electrode layer 310 and the lower electrode layer 320 will not be given. However, the signal transmission line 312 of the upper electrode layer 310 extends in the side-to-side direction of the upper electrode 311, and the signal transmission line 322 of the lower electrode layer 320 extends in the front-to-rear direction of the lower electrode 321. Consequently, the signal transmission line 312 of the upper electrode layer 310 is perpendicular to the signal transmission line 322 of the lower electrode layer 320, when the unit sensor is shown in a plan view.

The spacer layer 402 is disposed between the lower electrode layer 320 and the upper electrode layer 310. The spacer layer 402 is provided at a predetermined area thereof with an opening 404, through which the upper electrode 311 and the lower electrode 321 face each other. Consequently, the upper electrode 311 of the upper electrode layer 310 and the lower electrode 321 of the lower electrode layer 320 face each other through the opening 404 formed at the spacer layer 402, and the capacitance is changed depending upon the increase or decrease in the distance between the upper electrode 311 and the lower electrode 321.

Figure 30A:
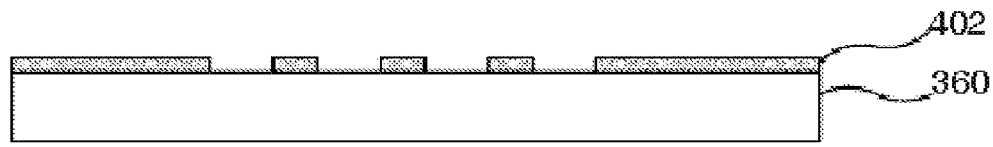
FIG. 30A is a sectional view schematically illustrating a method of manufacturing a spacer layer used in the unit sensor shown in FIGS. 29A and 29B.

FIG. 30A, in connection with FIGS. 29A and 29B, shows that the spacer layer 402 is prepared by applying liquid-state polymer to a silicon substrate 310, hardening the liquid-state polymer, forming a pattern using photolithography, forming the opening 404 through the polymer using dry etching, and removing the silicon substrate 360. When the photolithography is used to form the spacer layer 402 as described above, high resolution of below 1 mm is accomplished.

Referring back to FIGS. 29A and 29B, the insulating layer 410 is disposed between the upper electrode layer 310 and the spacer layer 402 to prevent the upper electrode 311 and the lower electrode 321 from contacting each other. The insulating layer 410 may be disposed between the lower electrode layer 320 and the spacer layer 402.

Figure 30B:
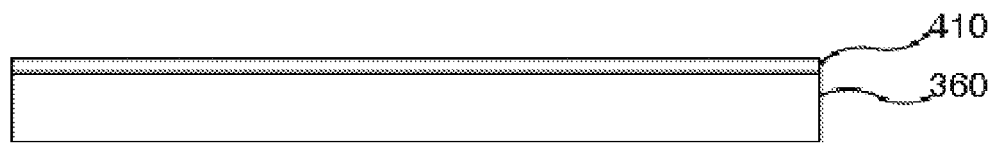
FIG. 30B is a sectional view schematically illustrating a method of manufacturing an insulating layer used in the unit sensor shown in FIGS. 29A and 29B.

FIG. 30B, in connection with FIGS. 29A and 29B, illustrates that the insulating layer 410 is prepared by applying liquid-state polymer to a silicon substrate 360, hardening the liquid-state polymer, and removing the silicon substrate 360.

Referring back to FIGS. 29A and 29B, the bump layer 400 is disposed on the upper electrode layer 310 such that pressure applied by a user can be reliably transmitted to the upper electrode layer 310.

Figure 30C:
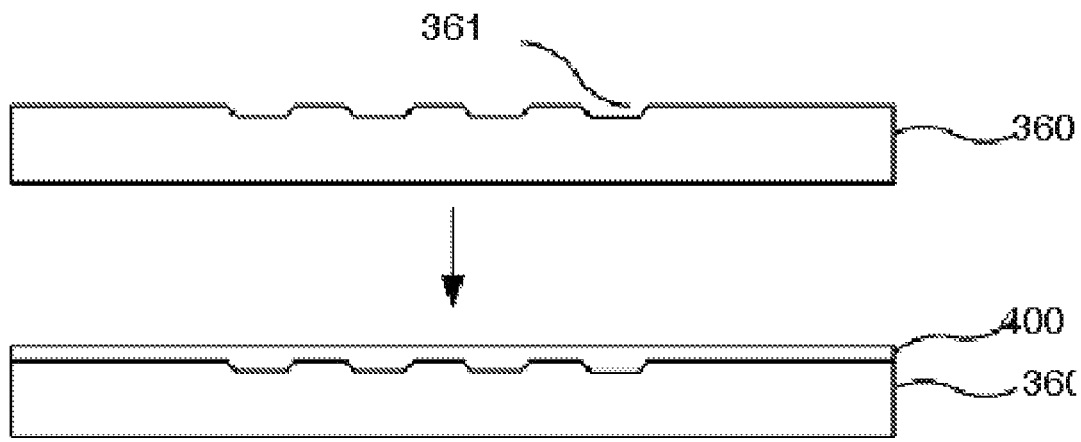
FIG. 30C is a sectional view schematically illustrating a method of manufacturing a bump layer used in the unit sensor shown in FIGS. 29A and 29B.

FIG. 30C, in connection with FIGS. 29A and 29B, shows that the bump layer 400 is prepared by etching the silicon substrate 360 to form a bump mold 361, applying liquid-state polymer to a silicon substrate 360, on which the bump mold 361 is formed, hardening the liquid-state polymer, and removing the silicon substrate 360.

Not only the substrates 312 and 323, which are used for the upper electrode layer 310 and the lower electrode layer 320, but also the spacer layer 402, the insulating layer 410, and the bump layer 400 may be made of polymer, such as silicon-based rubber or polyimide.

Figure 30D:
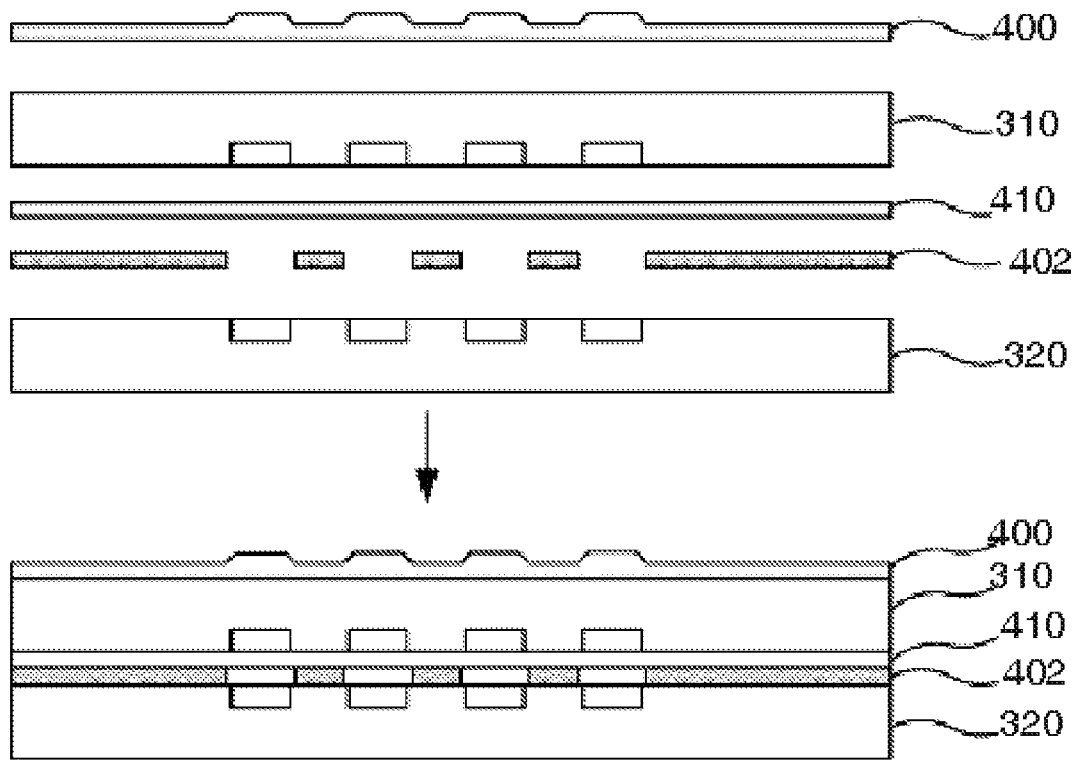
FIG. 30D is a sectional view schematically illustrating a method of manufacturing a unit sensor using the spacer layer, the insulating layer, and the bump layer shown in FIGS. 30A, 30B, and 30C, respectively.

Spacer layer 402, insulating layer 410, upper electrode layer 310, bump layer 400, and lower electrode layer 320, which are prepared as described above, are attached to each other, such that spacer layer 402, insulating layer 410, upper electrode layer 310, and bump layer 400 are sequentially stacked on the lower electrode layer 320, to manufacture the unit sensor as shown in FIG. 30D. Attachment of spacer layer 402, insulating layer 410, upper electrode layer 310, bump layer 400, and lower electrode layer 320 is not particularly restricted. For example, the surfaces of spacer layer 402, insulating layer 410, upper electrode layer 310, bump layer 400, and lower electrode layer 320 to be attached are treated using oxygen plasma, and are then aligned with each other. Subsequently, the surfaces are attached to each other, and then the attached surfaces are heated to a temperature of 60 degrees C. for approximately 50 minutes.

The operation of the unit sensor of FIGS. 29A and 29B can be as follows. When a user pushes the bump layer 400, the distance between the upper electrode 311 and the lower electrode 321 is decreased, and therefore, the capacitance between the upper electrode 311 and the lower electrode 321 is increased. As a result, a signal generated by the change of the capacitance is transmitted to an external circuit though the signal transmission line 322 connected between the external circuit and the lower electrode 321. When the pressure applied to the bump layer 400 is released, the distance between the upper electrode 311 and the lower electrode 321 is increased, and therefore, the capacitance between the upper electrode 311 and the lower electrode 321 is decreased. As a result, a signal generated by the change of the capacitance is transmitted to an external circuit though the signal transmission line 312 connected between the external circuit and the upper electrode 311.

Figure 31:
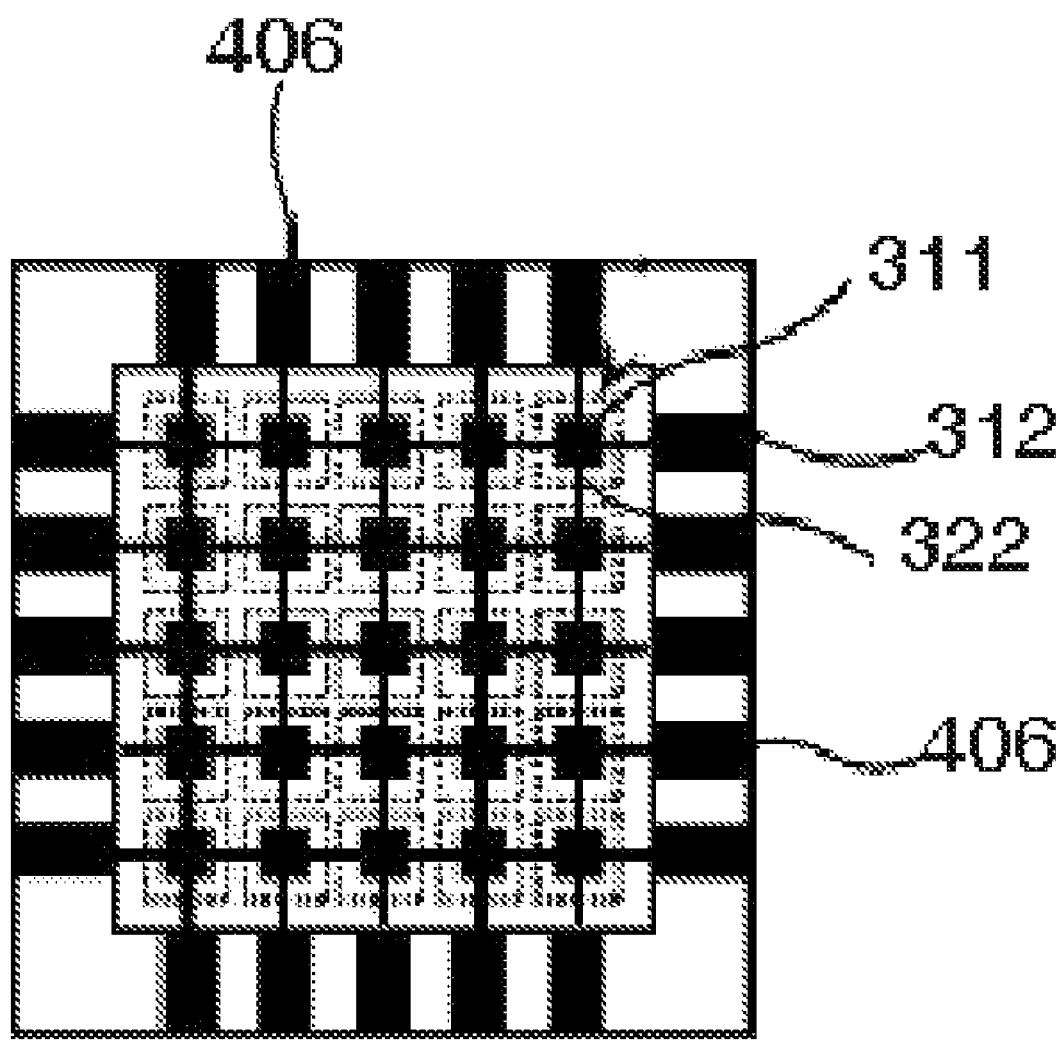
FIG. 31 is a plan view schematically illustrating a tactile sensor using the unit sensor shown in FIGS. 29A and 29B.

FIG. 31 shows a tactile sensor according to yet another embodiment of the present invention, comprising a unit sensor array including a plurality of unit sensors with the above-stated construction, which are arrayed in two dimensions, with edge conductors or connection lines 406.

The upper electrodes 311 of the unit sensors constituting the unit sensor array are electrically connected with each other by the sequential interconnection of the signal transmission lines 312 for the upper electrodes. The lower electrodes of the unit sensors constituting the unit sensor array are electrically connected with each other by the sequential interconnection of the signal transmission lines 322 for the lower electrodes. The connection lines 406 are disposed at the ends of the sequentially interconnected signal transmission lines 312 for the upper electrodes and the sequentially interconnected signal transmission lines 322 for the lower electrodes.

Figure 32:
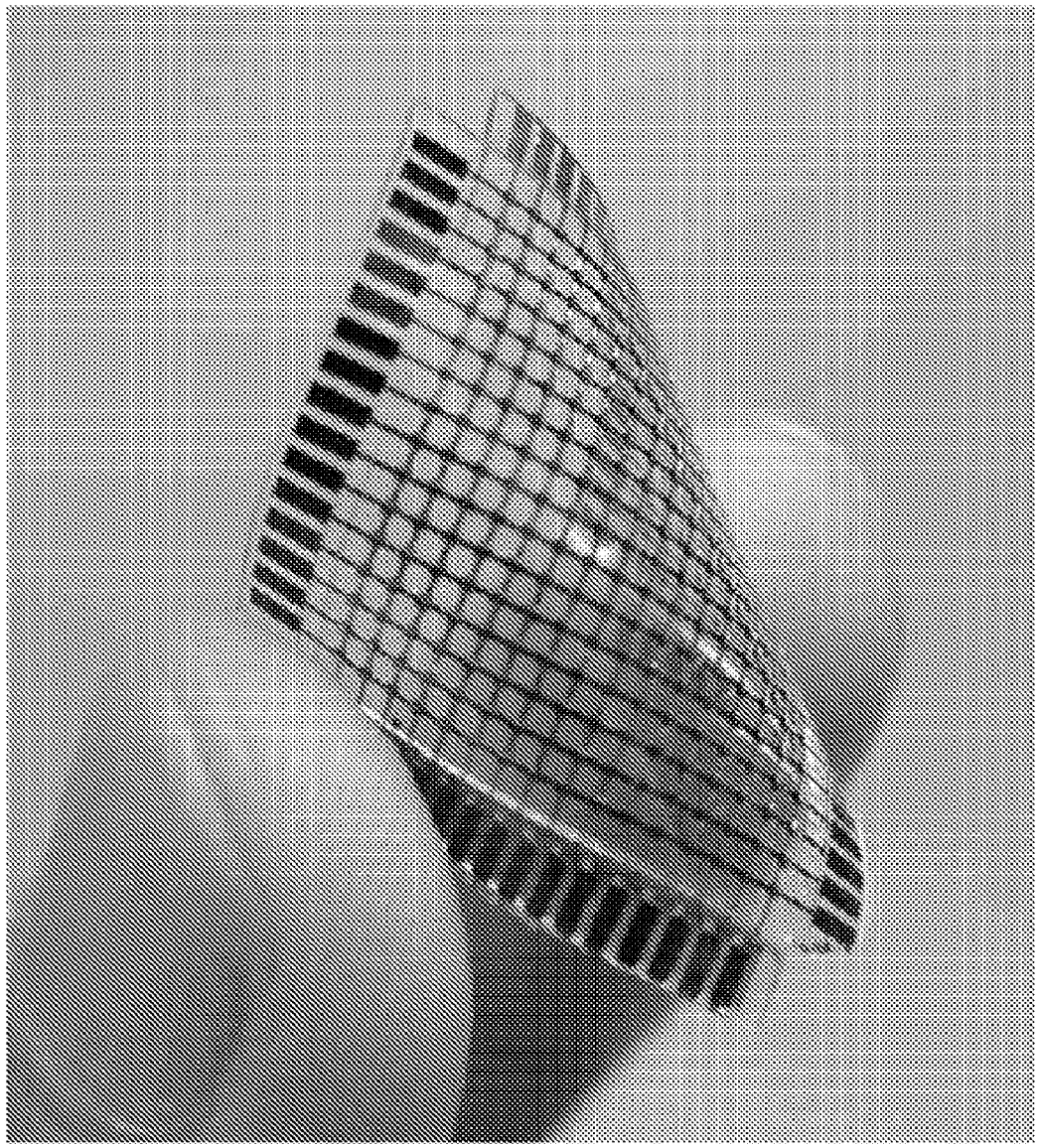
FIG. 32 is a photograph of the tactile sensor shown in FIG. 31.

FIG. 32 shows that the tactile sensor can have high flexibility.

As described above, the tactile sensor can be manufactured using the flexible unit sensors, and therefore, the tactile sensor can be very flexible. Furthermore, an extension to the tactile sensor can be easily accomplished using the connection lines.

Embodiments of the present invention can have the following aspects. In the electrode layer and the unit sensor, the substrate can be formed using liquid-state polymer. Consequently, the electrode layer and the unit sensor are very flexible and easily manufactured. In addition, photolithography is used to form the spacer layer of the unit sensor, and therefore, high resolution of below 1 mm is accomplished.

Consequently, the tactile sensor according to the present invention can be applied to the soles of shoes as well as robots.

In the case that the tactile sensor according to the present invention is applied to the soles of the shoes, the distribution of the pressure applied to the feet of a person when the person walks may be measured by the tactile sensor, and the measured data may be utilized medically. Also, the tactile sensor has soft tactile sensation. Consequently, the tactile sensor can provide various interfaces between a human and a computer as an extension to an input device, such as a mouse.

The above text has described several examples of various embodiments of the present invention. These examples and embodiments are meant to be illustrative, not restrictive, as all possible examples of the invention would be too numerous and cannot be included in this finite document. The scope of the invention is found in the claims which follow.

What is claimed is:

1. A flexible sensor fabric comprising:
a plurality of sensor modules, the sensor modules comprising a plurality of sensors for measuring a physical property and outputting a signal, a first flexible substrate for carrying the sensors and having edges, and a first plurality of conductor lines coupled to select and read the sensor signals;
where the sensor modules are arranged in a matrix forming rows and columns of adjacent sensor modules having the first plurality of conductor lines electrically coupled to the first plurality of conductors lines of the adjacent sensor modules,
the matrix having non-adjacent interposing sensor modules, the matrix having exterior matrix edges not coupled to sensor modules,
the sensor modules coupled such that sensors in non-adjacent sensor modules can be selected through interposing sensor modules and can have the sensor signals read through interposing sensor modules,
where the sensor modules are either directly electrically bonded to each other and/or electrically bonded through a flexible connection module.

2. The flexible sensor fabric of claim 1, in which at least some of the sensor modules are directly electrically coupled to each other with anisotropic conductive paste (ACP).

3. The flexible sensor fabric of claim 1, in which at least some of the sensor modules are indirectly coupled to each other through ACP bonding and flexible connection modules.

4. The flexible sensor fabric of claim 1, further comprising a plurality of circuit modules, the circuit modules comprising a second flexible substrate having edges, having at least one integrated circuit disposed thereon and having a second plurality of conductor lines coupled to the integrated circuit, where at least some of the circuit modules are disposed along the sensor module matrix exterior edges and electrically coupled to the sensor matrix first plurality of conductors to select the sensors for reading and to read out the selected sensor signals.

5. The flexible sensor fabric of claim 1, wherein the first flexible substrate comprises flexible polymer.

6. The flexible sensor fabric of claim 1, in which at least some of the sensors substantially differ from each other in the physical property measured and/or the range of the physical property measured.

* * * * *